United States Patent
Lin et al.

(10) Patent No.: US 11,524,965 B2
(45) Date of Patent: Dec. 13, 2022

(54) LONG-ACTING INJECTABLE FORMULATIONS AND CRYSTALLINE FORMS OF BUPRENORPHINE DERIVATIVES

(71) Applicant: Alar Pharmaceuticals Inc., Taichung (TW)

(72) Inventors: Tong-Ho Lin, Taichung (TW); Yung-Shun Wen, Taichung (TW); Jui-Wei Liang, Taichung (TW)

(73) Assignee: Alar Pharmaceuticals Inc., Taichung (TW)

( * ) Notice: Subject to any disclaimer, the term of this patent is extended or adjusted under 35 U.S.C. 154(b) by 0 days.

(21) Appl. No.: 16/981,745

(22) PCT Filed: May 10, 2019

(86) PCT No.: PCT/CN2019/086449
§ 371 (c)(1),
(2) Date: Sep. 17, 2020

(87) PCT Pub. No.: WO2019/214726
PCT Pub. Date: Nov. 14, 2019

(65) Prior Publication Data
US 2021/0122756 A1    Apr. 29, 2021

Related U.S. Application Data

(60) Provisional application No. 62/670,714, filed on May 11, 2018.

(51) Int. Cl.
| | | |
|---|---|---|
| *C07D 489/04* | (2006.01) | |
| *A61K 9/00* | (2006.01) | |
| *A61K 9/08* | (2006.01) | |
| *A61K 9/50* | (2006.01) | |
| *A61K 47/26* | (2006.01) | |
| *A61K 47/34* | (2017.01) | |

(52) U.S. Cl.
CPC ......... *C07D 489/04* (2013.01); *A61K 9/0019* (2013.01); *A61K 9/08* (2013.01); *A61K 9/5031* (2013.01); *A61K 47/26* (2013.01); *A61K 47/34* (2013.01); *C07B 2200/13* (2013.01)

(58) Field of Classification Search
CPC ...... C07D 489/04; A61K 9/0019; A61K 9/08; A61K 9/5031; A61K 47/26; A61K 47/34; C07B 220/13
See application file for complete search history.

(56) References Cited

FOREIGN PATENT DOCUMENTS

| | | | |
|---|---|---|---|
| WO | 2016/142877 | 9/2016 | |
| WO | WO-2016142877 A1 * | 9/2016 | .......... A61K 31/485 |

OTHER PUBLICATIONS

Audra Stinchcomb, Transdermal Delivery of Buprenorphine 3-Alkyl Ester Prodrugs for Treatment of Opioid Dependence, Doctoral Dissertation, University of Michigan https://www.proquest.com/dissertations-theses/transdermal-delivery-buprenorphine-3-alkyl-ester/docview/304201501/se-2?accountid=14753 (Year: 1995).*
Stinchcomb, et al, A Solubility and Related Physicochemical Property Comparison of Buprenorphine and its 3-Alkyl Esters, 12 Pharma. Res. 1526 (Year: 1995).*
Berrell, et al, Process Development Toward a Pro-Drug of Buprenorphine, 23 Org. Process. Res. Dev. 762 (Year: 2019).*
Vippagunta, et al, Crystalline Solids, 48 Adv. Drug Del. Rev. 3 (Year: 2001).*
International Search Report and Written Opinion for International Application No. PCT/CN2019/086449 dated Aug. 15, 2019, 8 pages.
Stinchcomb, et al. "A Solubility and Related Physicochemical Property Comparison of Buprenorphine and its 3-Alkyl Esters", Pharmaceutical Research, vol. 12, No. 10, Dec. 31, 1995, pp. 1526-1529.

* cited by examiner

*Primary Examiner* — Sean M Basquill
(74) *Attorney, Agent, or Firm* — Amin, Turocy & Watson, LLP

(57) ABSTRACT

This disclosure relates to crystalline forms of 3-acyl-buprenorphine derivatives and sustained release injectable pharmaceutical compositions for treatment of opioid dependence, pain or depression, including an aqueous suspension of crystalline 3-acyl-buprenorphrine, or a pharmaceutically acceptable salt thereof, wherein the composition does not include an organic solvent, a polylactide polymer, a polyglycolide polymer, or a copolymer of polylactide and polyglycolide. This disclosure also includes 3-acyl-buprenoprhine or a pharmaceutically acceptable salt thereof prepared in a controlled release matrix, including poly(lactide-co-glycolide), sucrose acetoisobutyrate, lecithin, diolein and a combination of two or more thereof.

8 Claims, 25 Drawing Sheets

LONG-ACTING INJECTABLE FORMULATIONS AND CRYSTALLINE FORMS OF BUPRENORPHINE DERIVATIVES

BACKGROUND

Technical Field

The present disclosure relates generally to crystalline forms and formulations of buprenorphine derivatives. In particular, the present disclosure relates to an injectable composition comprising buprenorphine derivatives, or the metabolite or prodrug thereof, its uses, as well as methods of treatment using the same for opioid dependence, pain, and depression.

Background

Buprenorphine, (5α,7α(s))-17-cyclopropylmethyl)-α-(1,1-dimethylethyl)-4,5-epoxy-18,19-dihydro-3-hydroxy-6-methoxy-α-methyl-6,14-ethenomorphinan-7-methanol, is a derivative of thebaine, which belongs to the family of opioid alkaloids. The structure of buprenorphine is shown by the following formula (Formula I) with a molecular weight of 467.64:

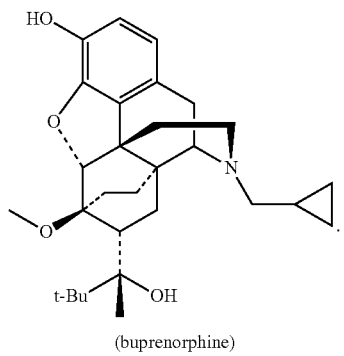

(buprenorphine)

Formula I

As a partial and potent μ-receptor agonist, buprenorphine has a higher affinity to compete with other full agonists, such as morphine, methadone, etc. With 25 to 40 times higher potency than that of morphine, buprenorphine is indicated for the treatment of moderate to severe chronic pain, and pre-operative analgesia in several dosage forms, e.g., Buprenex® (intramuscular or intravenous injection), Norspan®, Butrans® (a transdermal patch), Temgesic® (a sublingual tablet), and Belbuca® (a buccal film). The therapeutic concentrations ($C_{max}$) of Butrans in healthy subjects range from 0.1 to 0.5 ng/mL, corresponding to a dose of 5 to 20 μg/hour. In addition, various products of buprenorphine hydrochloride are approved for treating opioid addiction in higher dosages, e.g., Subutex (a sublingual tablet), Sublocade™ (a subcutaneous injection), and some are combination products of buprenorphine hydrochloride and naloxone hydrochloride, e.g., Suboxone® (a sublingual film, in a 4:1 ratio of buprenorphine hydrochloride and naloxone hydrochloride), Zubsoly® (a sublingual tablet), and Bunavail® (a buccal film). The therapeutic concentrations ($C_{max}$) of Suboxone range from 1 to 6 ng/mL, corresponding to a dose of 2 to 16 mg sublingual films.

Furthermore, buprenorphine is also a potent antagonist of the κ-opioid receptor, and this could result in the reduction of tolerance and has an antidepressant effect. Recently, buprenorphine is utilized in a combination product, ALK-5461, which consists of buprenorphine (a κ-receptor antagonist) and samidorphan (a μ-receptor agonist) and has been announced for an anti-depressant effect.

In previous studies, various buprenorphine derivatives were disclosed. Among them, modifications of the phenol group by forming ester bond linkages are more common. These ester derivatives are synthesized and compared with buprenorphine and the hydrochloride salt thereof. In 1995, Stinchcomb et al. published an article related to 3-alkyl ester derivatives of buprenorphine in *Pharm. Res.* (1995), 12, 1526-1529 (Formula II below, R=acetyl, propanoyl, butanoyl, pentanoyl, hexanoyl, heptanoyl). These derivatives were viewed as prodrugs and purported to improve the physiochemical characteristics of the parent compound to increase its relative permeability through skin in the following articles: *Biol. Pharm. Bull.* (1996), 19, 263-267 and *Pharm. Res.* (1996), 13, 1519-1523.

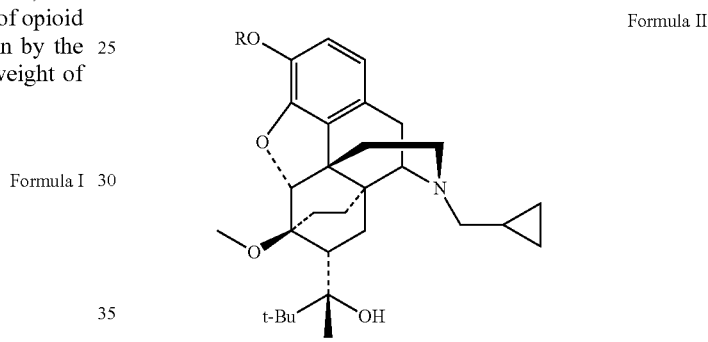

Formula II

Thereafter, several C3-esterfied buprenorphine derivatives and applications thereof have been disclosed in various patents. For example, U.S. Pat. No. 7,084,150, issued to Euro-Celtique S. A., describes a huge family of buprenorphine prodrugs and analogs, which include ester bonds or ether bond modified derivatives. EP Patent No. 1422230, issued to Jhi-Joung Wang, discloses dimerized derivatives of buprenorphine and similar alkylcarbonyl derivatives. Prodrug strategy and oil carrier of these derivatives were introduced by an intramuscular or subcutaneous injection, which displays prolonged analgesia actions for 5 hours to 96 hours.

A series of buprenorphine ester derivatives is also described in U.S. Pat. No. 7,964,610, issued to Reckitt Benckiser Healthcare (UK) Limited. Buprenorphine was modified with dicarboxylic acids or esters. Then, these derivatives were used for the treatment of opiate abuse/dependence and for the treatment of moderate to severe pain.

There are a variety of sustained release designs for buprenorphine indicated for the treatment of opioid dependence and chronic pain. For example, Titan Pharmaceuticals, Inc. developed a subcutaneous implant product of buprenorphine hydrochloride, Probuphine®, using their novel drug delivery system, ProNeura™, which is made from a mixture of ethylene vinyl acetate (EVA) and drug substance. Probuphine® is administrated once every six months through surgical implantation and removed from patients after treatment by surgical procedures.

Camurus established a novel drug delivery system, FluidCrystal®, which is based on lipid liquid crystals that are composed of phosphatidyl choline and glycerol dioleate.

The formulation disclosed in US Patent Application Publication No. 2013/0190341 is designed as a long-acting buprenorphine product to treat opioid dependence and chronic pain, and is administrated by subcutaneous injection weekly or monthly.

U.S. Patent Application Publication No. 2003/0152638, by Brookwood Pharmaceuticals, Inc., discloses an injectable slow-release microsphere formulation that comprises buprenorphine and poly(D,L-lactide). This formulation is able to treat heroin and alcohol abuse for a period of at least 28 days in a mammal.

U.S. Patent Application Publication No. 2014/0271869 (Oakwood Laboratories LLC) discloses a biodegradable formulation, which utilized their proprietary technology, Chroniject™. The platform is a polymer-based injectable microspheres system for drug delivery. The buprenorphine microspheres could be generated in higher drug load and claimed to achieve sustained release for at least one month to several months.

Indivior PLC (WO 2011/154724) developed a monthly depot, which employed Atrigel System to produce an injectable, flowable formulation for the treatment of opioid dependency. The composition includes a buprenorphine free base, biodegradable polymer, and a biocompatible solvent. The dissolved liquid could be injected and transformed in situ into a solid implant, providing 1-month and 3-month release profiles. In addition, suspension and solution designs are disclosed in WO 2011/154725 and WO 2015/136253, respectively. The suspension is composed of buprenorphine and polyethylene glycol polymer in aqueous conditions, providing a therapeutic period of between 7 and 30 days in dogs after a single intramuscular or subcutaneous injection. As for the disclosed solution, the composition consists of buprenorphine or a salt form thereof and a biocompatible organic solvent without a biodegradable polymer. After a single subcutaneous injection in beagle dogs, the formulation is able to provide at least a one-month therapeutic period.

Despite the fact that the prior pharmaceutical preparations described above are able to provide buprenorphine with extended release, there is still a need for formulation with better characteristics, such as a formulation without an organic solvent to diminish the risks of local site irritation, or a formulation having higher bioavailability, or a pharmacokinetic profile with smaller fluctuation and without a significant burst effect after one single injection.

SUMMARY

The present disclosure relates to various sustained-release pharmaceutical compositions of buprenorphine, or a prodrug, a pharmaceutically acceptable salt, and a metabolite thereof, including aqueous suspension of buprenorphine derivatives, and controlled release matrix, such as aqueous suspension of microspheres, poly(lactic-co-glycolic acid (PLGA)-based solutions, lipid-based formulations, and sucrose acetate isobutyrate-based formulations. The formulations of the present disclosure perform a therapeutically effective duration of at least one week to several months.

One aspect of the present disclosure relates to injectable suspension or the combination thereof, without utilizing an organic solvent. It is known that utilizing organic solvents in parenteral pharmaceutical preparations would enhance solubility, whereas the risks of local site irritation would inevitably increase. An injectable pharmaceutical composition in accordance with one embodiment of the present disclosure includes a suspension of crystalline 3-acyl-buprenorphine, or a pharmaceutically acceptable salt thereof, in a diluent comprising polyethylene glycol (PEG) polymer, polysorbate, and phosphate buffer saline, wherein the injectable pharmaceutical composition exhibits a steady release profile over a period of at least one week and a minimal risk of local site irritation following a single injection.

In accordance with embodiments of the present disclosure, long-acting suspension formulations are prepared from crystalline 3-acyl-buprenorphine derivatives. The acyl group is an alkylcarbonyl group. An alkyl portion of the alkylcarbonyl group is a straight-chain, or a branched-chain, having 1 to 17 carbon atoms.

In one embodiment, the present disclosure provides crystalline 3-acyl-buprenoprhine derivatives having x-ray powder diffraction patterns as follows:

| 3-Acyl-buprenoprhine derivatives | X-ray diffraction pattern (degrees 2θ) |
|---|---|
| Buprenorphine acetate | 4.70, 8.44, 9.38, 10.74, 12.42, 14.12, 17.72, 18.40, 18.78, 20.08, 20.56, 25.04, 26.88, 28.42, 28.46 |
| Buprenorphine pivalate | 5.93, 6.03, 9.08, 9.18, 9.33, 9.58, 9.68, 10.83, 10.93, 11.03, 12.18, 12.28, 12.78, 12.88, 12.98, 15.58, 15.73, 15.83, 15.98, 17.38, 17.53, 18.18, 18.28, 18.38, 19.43, 27.73, 27.83, 29.18 |
| Buprenorphine pentanoate | 2.33, 5.73, 5.83, 5.98, 6.13, 9.33, 9.43, 9.53, 9.63, 9.98, 10.08, 10.18, 11.83, 11.93, 12.03, 12.53, 12.68, 12.83, 12.98, 13.08, 15.73, 15.88, 16.03, 16.38, 18.28, 18.38, 18.58, 19.28, 19.43, 22.23 |
| Buprenorphine hexanoate | 2.33, 7.53, 8.13, 9.05, 10.93, 11.08, 12.93, 13.13, 13.38, 13.48, 15.88, 16.03, 17.18, 17.28, 17.73, 17.93, 21.13, 21.23, 21.33 |
| Buprenorphine decanoate | 5.80, 8.00, 10.50, 11.50, 11.60, 13.82, 14.44, 14.96, 16.06, 17.34, 18.32, 18.58, 18.98, 19.44, 20.92, 23.06, 23.40, 24.22, 24.38, 24.92 |
| Buprenorphine dodecanoate | 5.68, 8.03, 9.88, 9.98, 10.93, 11.38, 11.48, 17.13, 17.23, 17.33, 18.18, 18.28, 18.38, 18.93, 19.13, 19.23, 19.53, 21.03 |

In accordance with embodiments of the present disclosure, it relates to aqueous suspension, wherein the 3-acyl-buprenorphine, or a pharmaceutically acceptable salt thereof, is present at a concentration of 1-99% w/v, 5-90% w/v, 5-60% w/v, or 10-30% w/v.

In accordance with embodiments of the present disclosure, it relates to controlled release matrix formulations. The biocompatible organic solvent utilized in PLGA-based formulations, lipid-based formulations, and sucrose acetate isobutyrate-based formulations is N-methyl-2-pyrrolidone, ethyl acetate, ethanol, butanol, 2-butanol, isobutanol, isopropanol, glycerin, benzyl benzoate, dimethyl sulfoxide, N,N-dimethylacetamide, propylene glycol, dimethyl glycol, benzyl alcohol, an ester, an ether, an amide, a carbonate, a lactam, a sulfonyl, or any combination thereof.

In accordance with embodiments of the present disclosure, an injectable pharmaceutical composition may further comprise a preservative. In accordance with embodiments of the present disclosure, the preservative is selected from the group consisting of methylparaben, propylparaben and benzylalcohol.

In accordance with embodiments of the present disclosure, an injectable pharmaceutical composition is formulated for subcutaneous, intramuscular or intradermal injection.

Another aspect of the present disclosure relates to methods for treating opioid addiction, pain, or depression. A method in accordance with one embodiment of the present disclosure comprises administering to a subject in need thereof a therapeutically effective amount of the injectable pharmaceutical composition according to any embodiments described above.

In accordance with embodiments of the present disclosure, the administering is performed at a frequency of once per week, once per month, or once every three months.

Other aspects of the present disclosure will become apparent with the attached drawings and the following detailed descriptions.

DETAILED DESCRIPTION

Figure 1:
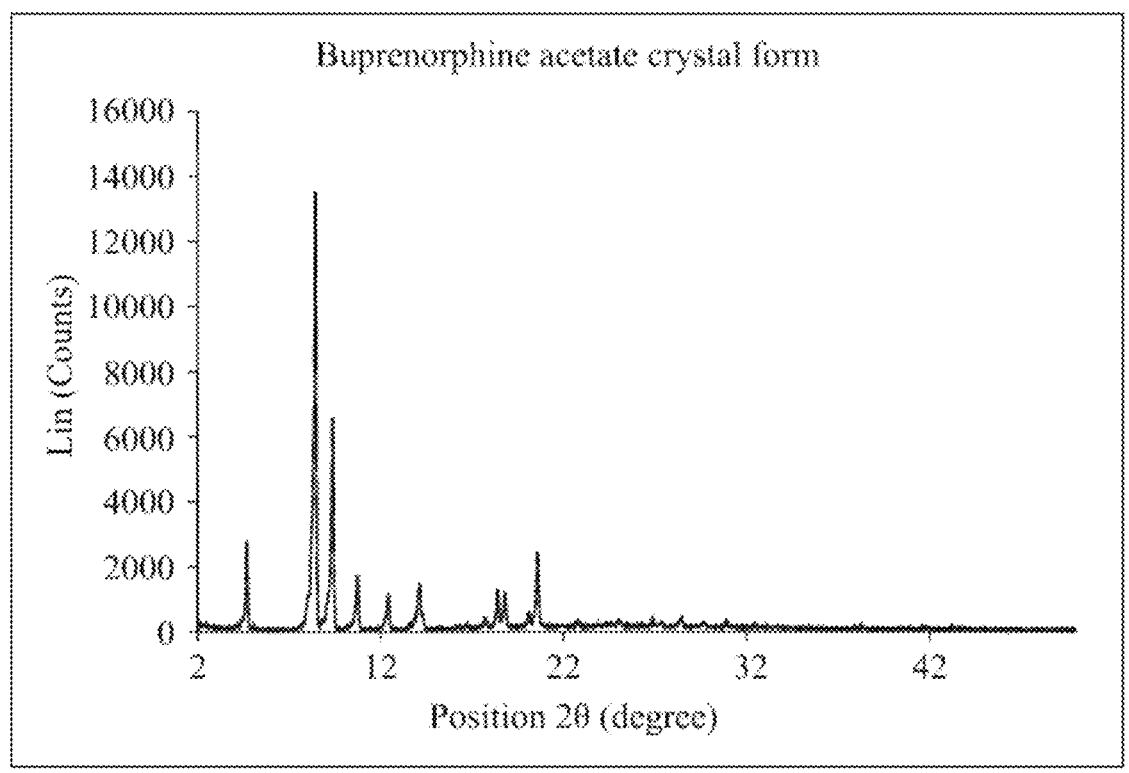
FIG. 1 illustrates the X-ray powder diffraction pattern of buprenorphine acetate crystal form.

Embodiments of the present disclosure relate to formulations of buprenorphine derivatives in the forms of aqueous suspension of crystalline buprenorphine derivatives, aqueous suspension of microspheres, PLGA-based solutions, lipid-based formulations, and sucrose acetate isobutyrate-based formulations, having long-lasting release profiles after single dose administration and displaying minimal initial bursts for the treatment of opioid addiction, pain or depression. In accordance with embodiments of the present disclosure, the buprenorphine derivatives are 3-alkyl ester derivatives, i.e., esters formed between the 3-hydroxy (phenol) group of buprenorphine and alkylcarbonylation (acylation) reagents.

In accordance with embodiments of the present disclosure, an alkylcarbonyl reagent (R—CO—X), wherein R is an alkyl residue, may be an acyl chloride, an acyl anhydride, or an acyl active ester. The alkyl portion of an alkylcarbonyl group may be a straight-chain or branched alkyl group. The alkyl portion may contain any suitable number of carbons, such as 1-18 ($C_1$-$C_{18}$), 1-16 ($C_1$-$C_{16}$), 1-12 ($C_1$-$C_{12}$), 1-10 ($C_1$-$C_{10}$), 1-5 ($C_1$-$C_5$), or 1-3 ($C_1$-$C_3$). Examples of alkylcarbonyl (acyl) groups may include acetyl, propionyl, butyryl, pentanyl, hexanyl, decanyl, stearyl, and palmityl.

In accordance with embodiments of the present disclosure, the buprenorphine derivatives may be synthesized using conventional methods. Buprenorphine or its salt can be purchased from several commercial sources, such as Sigma-Aldrich. To prepare a buprenorphine derivative, buprenorphine (or its salt) may be reacted with an acyl chloride in the presence of a base (e.g., triethylamine) to form an ester bond. The product (3-acyl-buprenorphine or 3-alkylcarbonyl-buprenorphine) may be purified with conventional methods (e.g., column chromatography).

As used in this description, a buprenorphine derivative refers to 3-acyl-buprenorphine (3-alkylcarbonyl-buprenorphine) or a salt thereof. A buprenorphine derivative of the present disclosure may function as a prodrug, which may be converted into the parent compound, buprenorphine.

The crystalline buprenorphine derivatives were further characterized by X-ray diffraction (XRD), differential scanning calorimeters (DSC), nuclear magnetic resonance spectroscopy (NMR), and infrared spectroscopy (IR).

A formulation of the present disclosure may comprise a 3-acyl-buprenorphine derivative suspended in an aqueous diluent containing PEG polymer, polysorbate, and phosphate buffer saline. The aqueous suspended formulation may contain the buprenorphine derivative or a salt thereof in any suitable concentration, such as 1-99% w/v, 1-90% w/v, 5-90% w/v, 5-80% w/v, 10-70% w/v, or 10-60% w/v. It is noted that when a numerical range is disclosed in this description, it is intended to include all numbers within the ranges, as if each of these numbers have been individually disclosed.

A formulation of the present disclosure may further comprise another pharmaceutically acceptable excipient, carrier, diluent, or preservative. In accordance with embodiments of the present disclosure, a preservative may be selected from the group consisting of methylparaben, propylparaben and benzylalcohol.

A formulation of the present disclosure may comprise of microspheres of 3-acyl-buprenorphine derivative or a salt form thereof and an aqueous diluent containing phosphate-buffered saline, sodium carboxymethylcellulose, and polysorbate. The thermoplastic polymer utilized for microspheres may be a polylactide, a polyglycolide, a 50/50, 55/45, 60/40, 65/35, 70/30, 75/25, 80/20, 85/15, 90/10 or 95/5 poly(DL-lactic-co-glycolide) with a carboxyl terminal group or an ester terminated group or a combination thereof.

A formulation of the present disclosure may comprise of 3-acyl-buprenorphine derivative or a salt form thereof, thermoplastic polymer, and one or more suitable biocompatible solvents. The buprenorphine derivative may be in the form of a free base or a pharmaceutically acceptable salt thereof, such as a salt of HCL, formate, acetate, citric acid or the like. The thermoplastic polymer may be a polylactide, a polyglycolide, a 50/50, 55/45, 60/40, 65/35, 70/30, 75/25, 80/20, 85/15, 90/10 or 95/5 poly(DL-lactic-co-glycolide) with a carboxyl terminal group or an ester terminated group or a combination thereof. The biocompatible solvents may be organic solvents, such as N-methyl-2-pyrrolidone (NMP), ethyl acetate (EtOAc), ethanol (EtOH), butanol, 2-butanol, isobutanol, glycerin, benzyl benzoate (BnBzO), dimethyl sulfoxide, propylene glycol, dimethyl glycol, and benzyl alcohol.

A formulation of the present disclosure may comprise 3-acyl-buprenorphine derivative or a salt form thereof dissolved in a lipid-based solution comprising lecithin, diolein and biocompatible solvents. The biocompatible solvents may be organic solvents, such as N-methyl-2-pyrrolidone (NMP), ethyl acetate (EtOAc), ethanol (EtOH), butanol, 2-butanol, isobutanol, glycerin, benzyl benzoate (BnBzO), dimethyl sulfoxide, propylene glycol, dimethyl glycol, and benzyl alcohol.

A formulation of the present disclosure may comprise an ionic complex of 3-acyl-buprenorphine derivative or a salt form thereof, sucrose acetate isobutyrate (SAIB) dissolved or suspended in a biocompatible solvent. The biocompatible solvents may be organic solvents, such as N-methyl-2-pyrrolidone (NMP), ethyl acetate (EtOAc), ethanol (EtOH), butanol, 2-butanol, isobutanol, glycerin, benzyl benzoate (BnBzO), dimethyl sulfoxide, propylene glycol, dimethyl glycol, and benzyl alcohol.

The various formulations of the present disclosure do not have undesirable initial burst and may display a sustained releasing profile over 1 week, 2 weeks, 3 weeks, 1 month, 2 months, 3 months, 4 months, 5 months, 6 months or longer. The formulations without the significant burst release of buprenorphine may not only reduce the risks of several systemic adverse effects, e.g., pinpoint pupils, sedation, hypotension, and respiratory depression, but also lessen the burden of physicians to monitor patients frequently. Furthermore, the aqueous suspension formulation of the buprenorphine derivative without an organic solvent exhibits high bioavailability, pharmaceutically effective plasma concentration for at least one week, and minimal risk of local site reactions.

Embodiments of the present disclosure will be further illustrated with the following examples. However, one skilled in the art would appreciate that these examples are for illustration only and that other modifications and variations are possible without departing from the scope of the disclosure.

EXAMPLE 1

Synthesis of 3-acyl-buprenorphine Derivatives

The following description is the procedure for synthesis of 3-acyl-buprenorphine derivatives. To a suitable 3-necked round bottom flask, buprenorphine HCl and dichloromethane (DCM) were added for a suspension, which was placed in an ice bath for cooling. Afterwards, trimethylamine (TEA) was added slowly with stirring. Acyl chloride was then added dropwise into the flask. The ice bath was revoked after all the materials were added. The reaction mixture was carried out at ambient temperature for 1 to 4 hours. The reaction mixture was neutralized with saturated sodium bicarbonate aqueous solution. The organic layer was washed with brine and then dried with sodium sulfate. After condensation under reduced pressure, the crude buprenorphine derivative was obtained. (Table 1)

TABLE 1

| Synthesis condition of various 3-acyl-buprenorphine derivatives | | | | |
|---|---|---|---|---|
| Entry | Buprenorphine HCl | Acyl chloride | Base | Solvent |
| 1-1 | 20.00 g, 39.7 mmol | Acetyl chloride (3.74 g, 47.6 mmol) | TEA (8.03 g, 79.3 mmol) | DCM (200 mL) |
| 1-2 | 1.00 g, 1.98 mmol | Trimethylacetyl chloride (0.29 mL, 2.38 mmol) | TEA (0.4 g, 3.96 mmol) | DCM (10 mL) |
| 1-3 | 1.00 g, 1.98 mmol | Valeroyl chloride (0.28 mL, 2.38 mmol) | TEA (0.4 g, 3.96 mmol) | DCM (10 mL) |

TABLE 1-continued

Synthesis condition of various 3-acyl-buprenorphine derivatives

| Entry | Buprenorphine HCl | Acyl chloride | Base | Solvent |
|---|---|---|---|---|
| 1-4 | 2.0 g, 3.97 mmol | Hexanoyl chloride (0.64 g, 4.76 mmol) | TEA (0.8 g, 7.93 mmol) | DCM (20 mL) |
| 1-5 | 10.00 g, 19.84 mmol | Decanoyl chloride (4.54 g, 23.8 mmol) | TEA (5.53 mL, 39.68 mmol) | DCM (100 mL) |
| 1-6 | 1.00 g, 1.98 mmol | Dodecanoyl chloride (0.52 g, 2.38 mmol) | TEA (0.4 g, 3.95 mmol) | DCM (10 mL) |

EXAMPLE 2

Crystallization of 3-acyl-buprenorphine Derivatives

Following is the crystallization procedure of 3-acyl-buprenorphine derivatives. The crude 3-acyl-buprenorphine derivatives were dissolved in the solvents described in Table 2 at ambient temperature or heated oil or eater bath. Then, the dissolved mixtures were cooled with ice bath to form crystalline 3-acyl-buprenorphine derivatives.

TABLE 2

Crystallization condition of 3-acyl-buprenorphine derivatives

| Entry | Crude Compound | Solvent composition | Temperature |
|---|---|---|---|
| 2-1 | Buprenorphine acetate, 9.6 g | Ethanol (95%, 90 mL) | 60° C. water bath to dissolve, gradually cooled to ambient temperature |
| 2-2 | Buprenorphine decanoate, 17.51 g | Anhydrous ethanol (99.5%, 260 mL) | 51° C. oil bath to dissolve, gradually cooled to ambient temperature |
| 2-3 | Buprenorphine decanoate, 12.35 g | Ethanol (95%, 100 mL) | 56° C. oil bath to dissolve, gradually cooled to ambient temperature |
| 2-4 | Buprenorphine decanoate, 1.0 g | Isopropanol (10 mL) | 59° C. water bath to dissolve, gradually cooled to ambient temperature |
| 2-5 | Buprenorphine decanoate, 1.0 g | N-methyl-2-pyrrolidone (NMP, 3 mL) | 53° C. water bath to dissolve, cooled with ice bath |
| 2-6 | Buprenorphine decanoate, 0.5 g | Acetonitrile (ACN, 7.5 mL) | 58° C. water bath to dissolve, gradually cooled to ambient temperature |
| 2-7 | Buprenorphine pivalate, 1.15 g | Ethanol (95%, 11 mL) | 60° C. water bath to dissolve, cooled with ice bath |
| 2-8 | Buprenorphine pentanoate, 1.2 g | Ethanol (95%, 12 mL) | 60° C. water bath to dissolve, cooled with ice bath |
| 2-9 | Buprenorphine hexanoate, 1.7 g | Ethanol (95%, 17 mL) | Dissolved at ambient temperature, cooled with ice bath |
| 2-10 | Buprenorphine dodecanoate, 1.38 g | Ethanol (95%, 13.8 mL) | 60° C. water bath to dissolve, cooled with ice bath |

The crystalline 3-acyl-buprenorphine derivatives obtained were characterized by XRD, DSC, NMR and IR.

Figure 2:
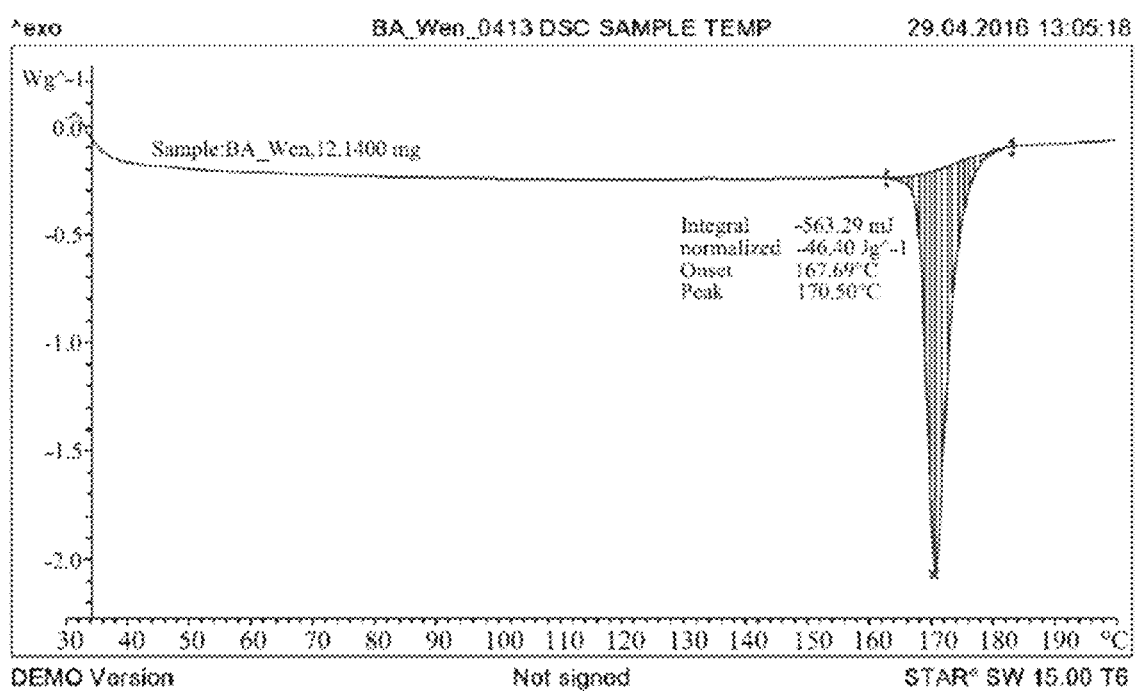
FIG. 2 illustrates the differential scanning calorimetry (DSC) pattern of buprenorphine acetate crystal form.
Figure 3:
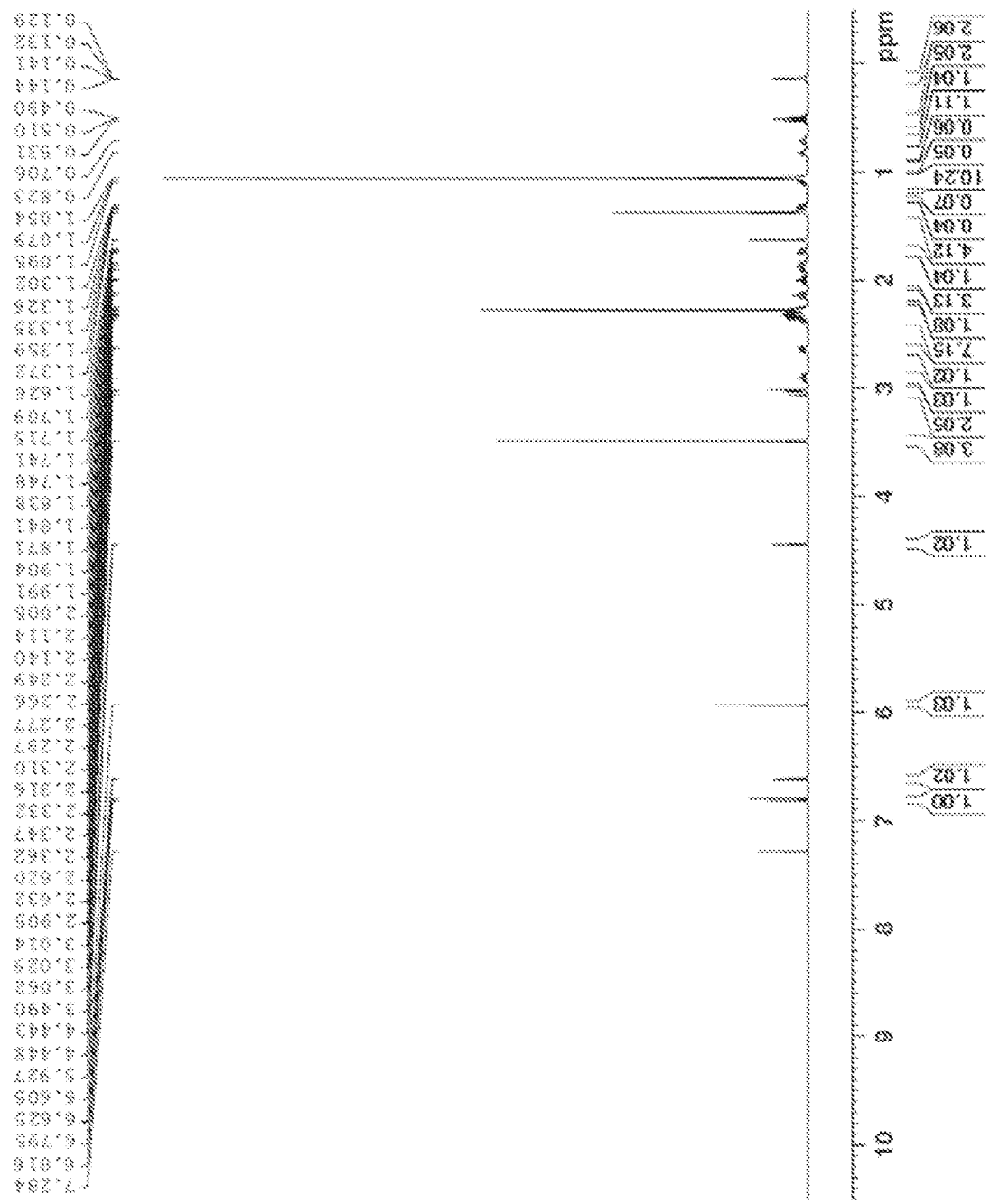
FIG. 3 illustrates the $^1$H nuclear magnetic resonance (NMR) spectrum of buprenorphine acetate crystal form.
Figure 4:
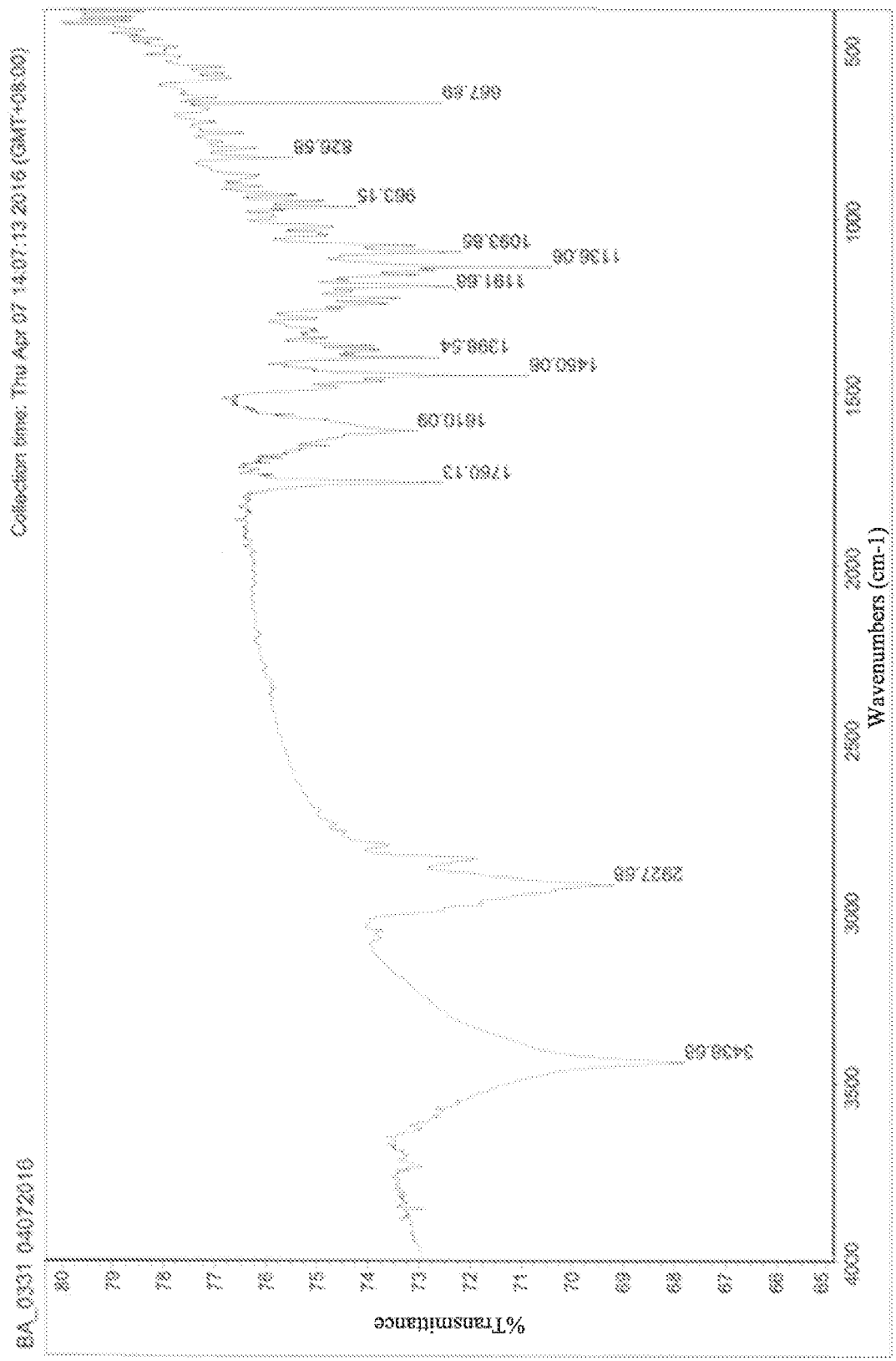
FIG. 4 illustrates the Fourier-transform infrared spectroscopy (FTIR) spectrum of buprenorphine acetate crystal form.

The crystal form of buprenorphine acetate was characterized by X-ray diffraction pattern (Bruker, D8 DISCOVER SSS Multipurpose Thin-film X-ray Diffractometer) having peaks at 4.70, 8.44, 9.38, 10.74, 12.42, 14.12, 17.72, 18.40, 18.78, 20.08, 20.56, 25.04, 26.88, 28.42, 28.46 degrees 2θ (FIG. 1), and its melting point was determined to be 167.69° C. by differential scanning calorimetry, DSC (Mettler-Toledo, TGA/DSC 3+ STARe System) (FIG. 2). The structure of the buprenorphine acetate crystal form was confirmed with Nuclear Magnetic Resonance, NMR (Bruker, Ascend™ 400 MHz) and Fourier Transform Infrared Spectroscopy, FTIR (Thermo, Nicolet-IS10 Mattson Satellite-5000 spectrometer) (FIGS. 3 and 4). Representative $^1$H NMR (400 MHz, CDCl$_3$): 6.81 (d, 1H, J=8.4 Hz), 6.62 (d, 1H, J=8.0 Hz), 5.93 (s, 1H), 4.45 (s, 1H), 3.49 (s, 3H), 3.03 (m, 2H), 2.94-2.81 (m, 1H), 2.64 (dd, 1H, J=4.8, 12.0 Hz), 2.40-2.24 (m, 7H), 2.14 (t, 1H, J=10.0 Hz), 2.04-1.78 (m, 3H), 1.77-1.68 (dd, 1H, J=2.8, 13.2 Hz), 1.42-1.38 (m, 4H), 1.15-1.01 (m, 10H), 0.89-0.77 (m, 1H), 0.77-0.65 (m, 1H), 0.51 (m, 2H), 0.14 (m, 2H). FTIR absorption band (cm$^{-1}$): 3439, 2928, 1760, 1610, 1450, 1399, 1192, 1136, 1094, 963, 827, 668 (±1 cm$^{-1}$).

Figure 5:
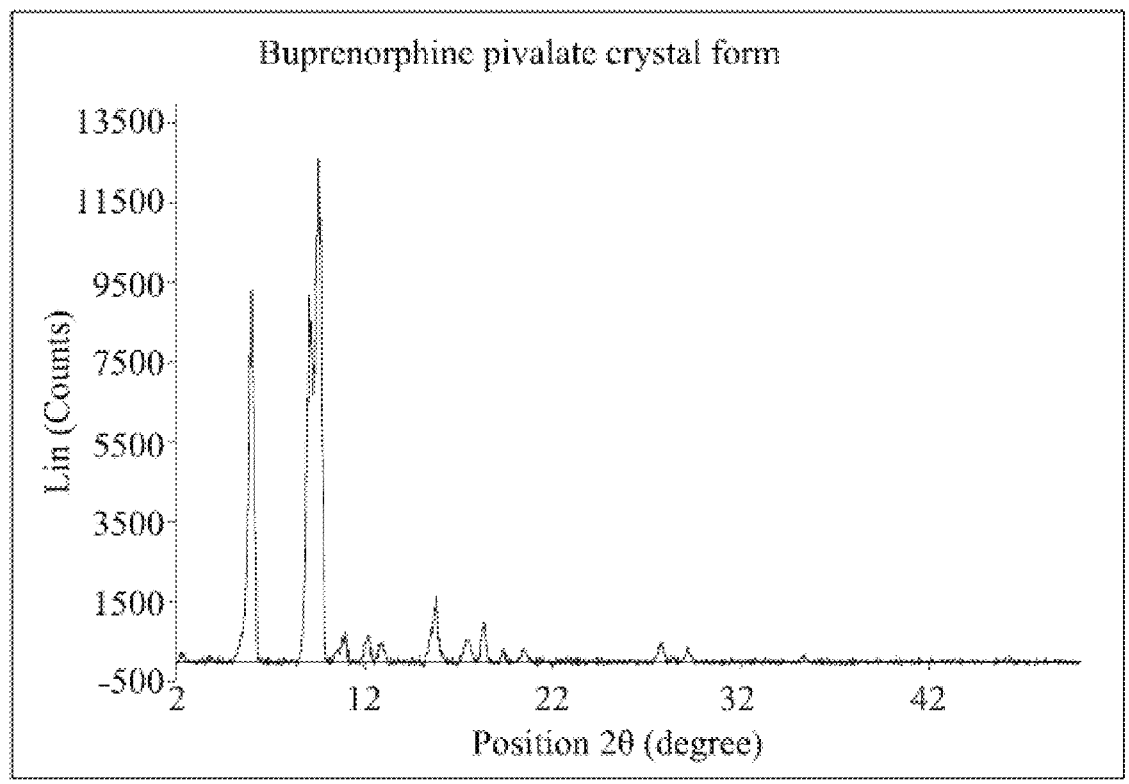
FIG. 5 illustrates the X-ray powder diffraction pattern of buprenorphine pivalate crystal form.
Figure 6:
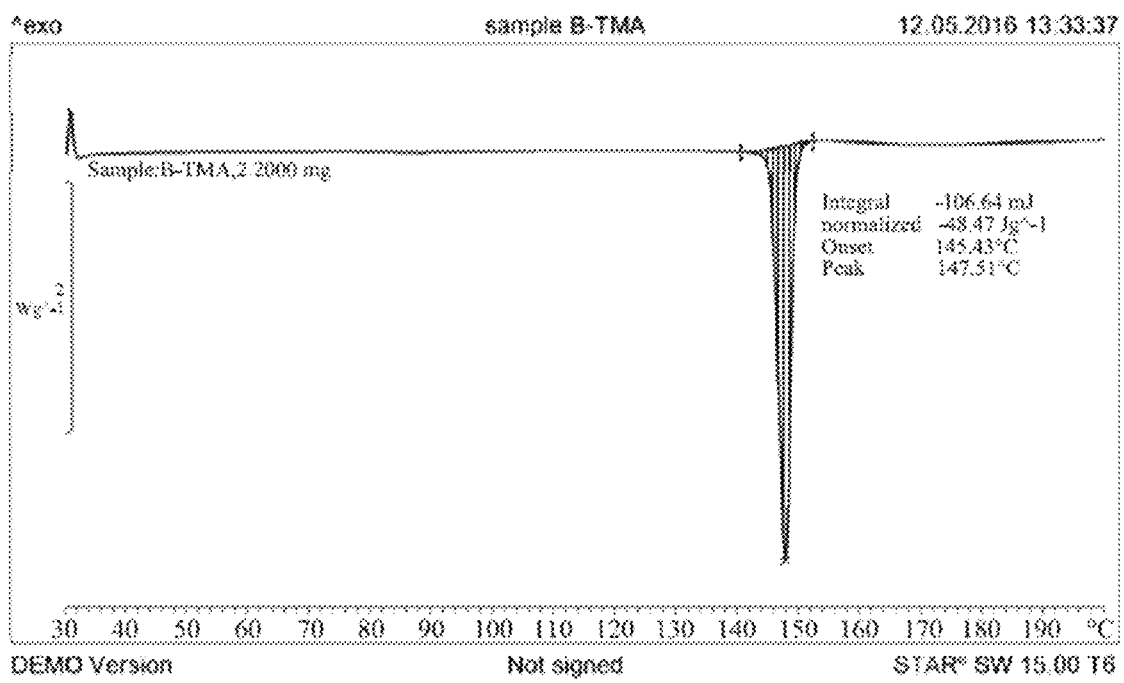
FIG. 6 illustrates the DSC pattern of buprenorphine pivalate crystal form.
Figure 7:
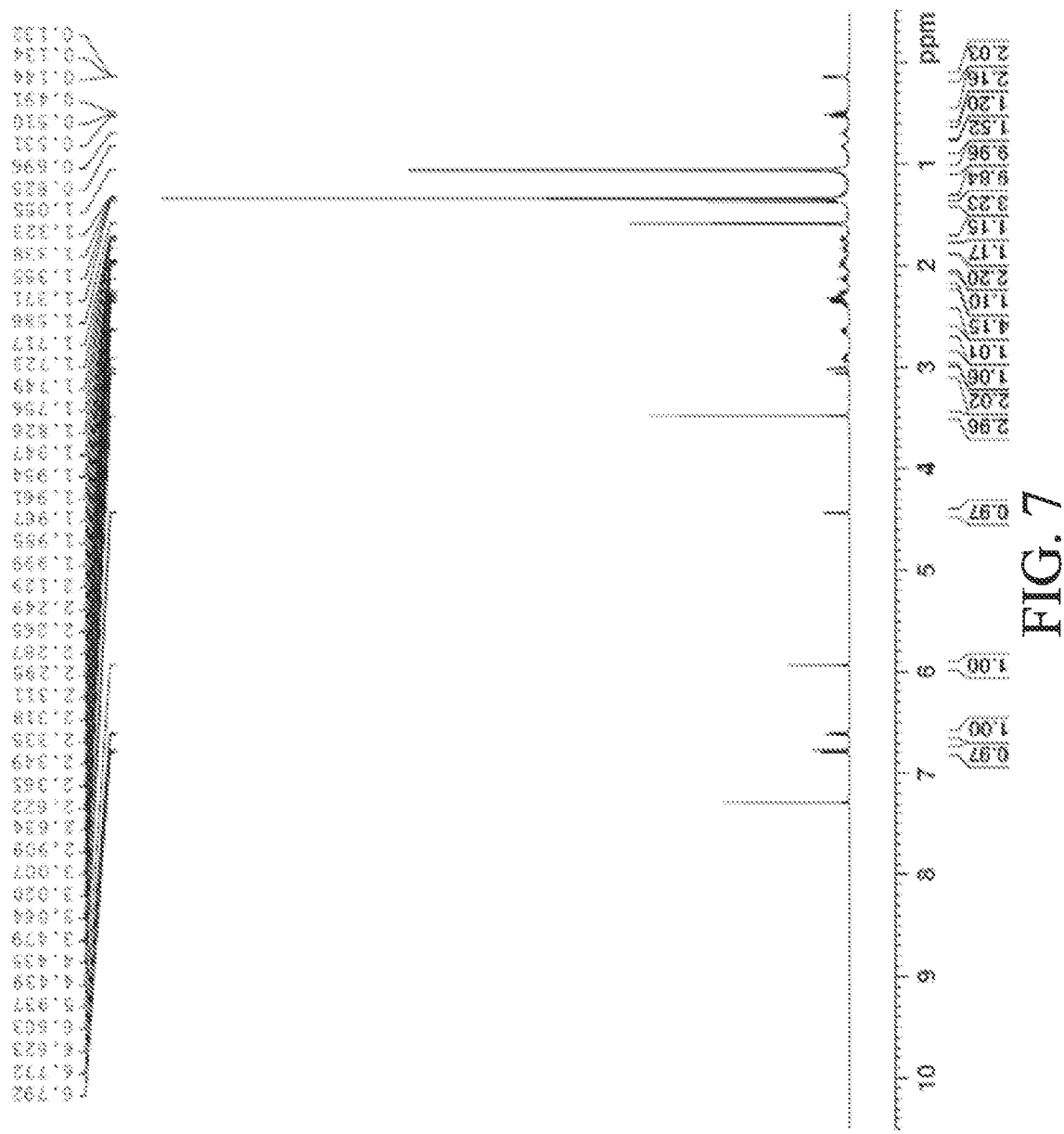
FIG. 7 illustrates the $^1$H NMR spectrum of buprenorphine pivalate crystal form.
Figure 8:
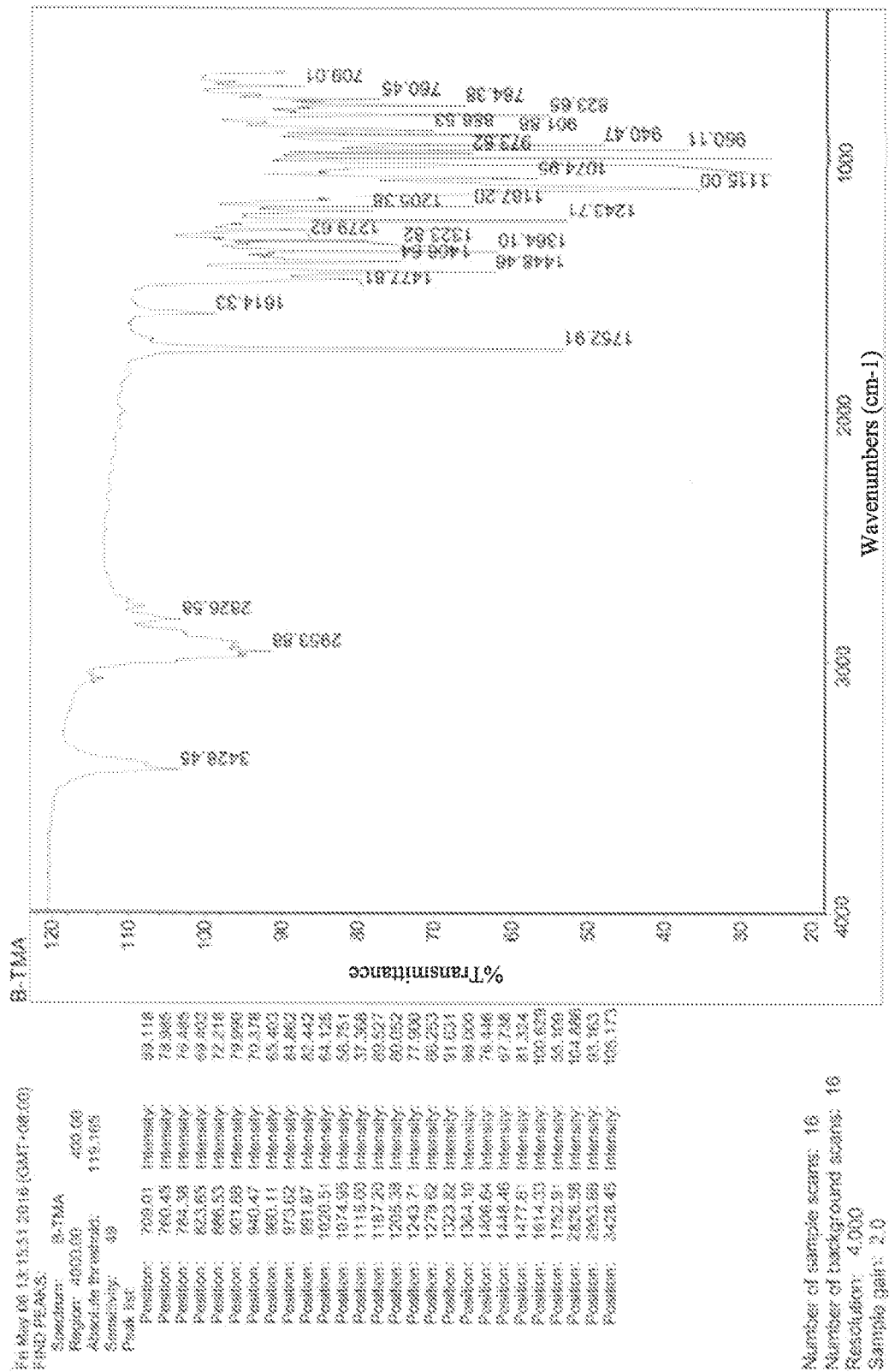
FIG. 8 illustrates the FTIR spectrum of buprenorphine pivalate crystal form.

The crystal form of buprenorphine pivalate was characterized by X-ray diffraction pattern (PHILIPS X'PERT Pro, PHILIPS X'PERT Pro MPD) having peaks at 5.93, 6.03, 9.08, 9.18, 9.33, 9.58, 9.68, 10.83, 10.93, 11.03, 12.18, 12.28, 12.78, 12.88, 12.98, 15.58, 15.73, 15.83, 15.98, 17.38, 17.53, 18.18, 18.28, 18.38, 19.43, 27.73, 27.83, 29.18 degrees 2θ (FIG. 5), and its melting point was determined to be 145.43° C. by means of differential scanning calorimetry, DSC (Mettler-Toledo, TGA/DSC 3+ STARe System) (FIG. 6). The structure of the buprenorphine pivalate crystal form was identified with Nuclear Magnetic Resonance, NMR (Bruker, Ascend™ 400 MHz) and Fourier Transform Infrared Spectroscopy, FTIR (Thermo, Nicolet-IS10 Mattson Satellite-5000 spectrometer). (FIGS. 7 and 8). Representative $^1$H NMR (400 MHz, CDCl$_3$): 6.78 (d, 1H, J=8.0 Hz), 6.61 (d, 1H, J=8.0 Hz), 5.94 (s, 1H), 4.44 (d, 1H, J=1.6 Hz), 3.48 (s, 3H), 3.04 (m, 2H), 2.91 (m, 1H), 2.64 (dd, 1H, J=4.8, 12.0 Hz), 2.42-2.20 (m, 4H), 2.13 (t, 1H, J=10.0 Hz), 2.05-1.89 (m, 2H), 1.89-1.68 (m, 2H), 1.37 (s, 3H), 1.34 (m, 10H), 1.06 (m, 10H), 0.82 (m, 1H), 0.69 (m, 1H), 0.51 (m, 2H), 0.14 (m, 2H). FTIR absorption band (cm$^{-1}$): 3428, 2954, 2827, 1753, 1614, 1478, 1448, 1407 (±1 cm$^{-1}$).

Figure 9:
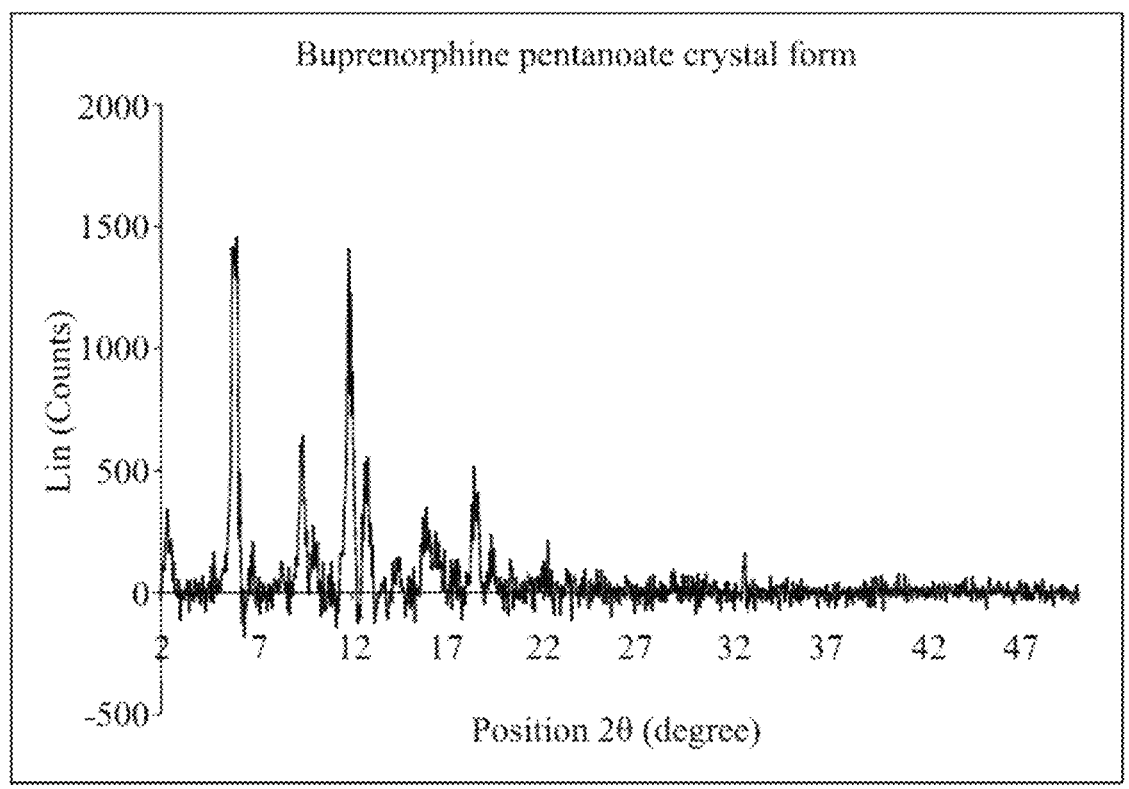
FIG. 9 illustrates the X-ray powder diffraction pattern of buprenorphine pentanoate crystal form.
Figure 10:
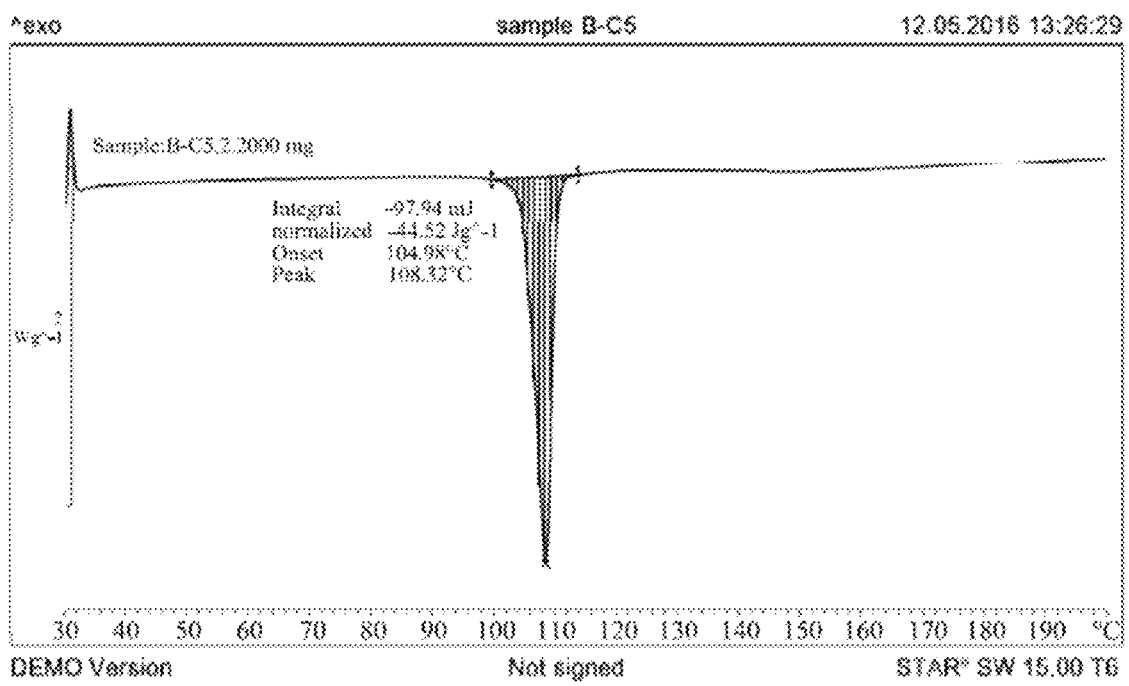
FIG. 10 illustrates the DSC pattern of buprenorphine pentanoate crystal form.
Figure 11:
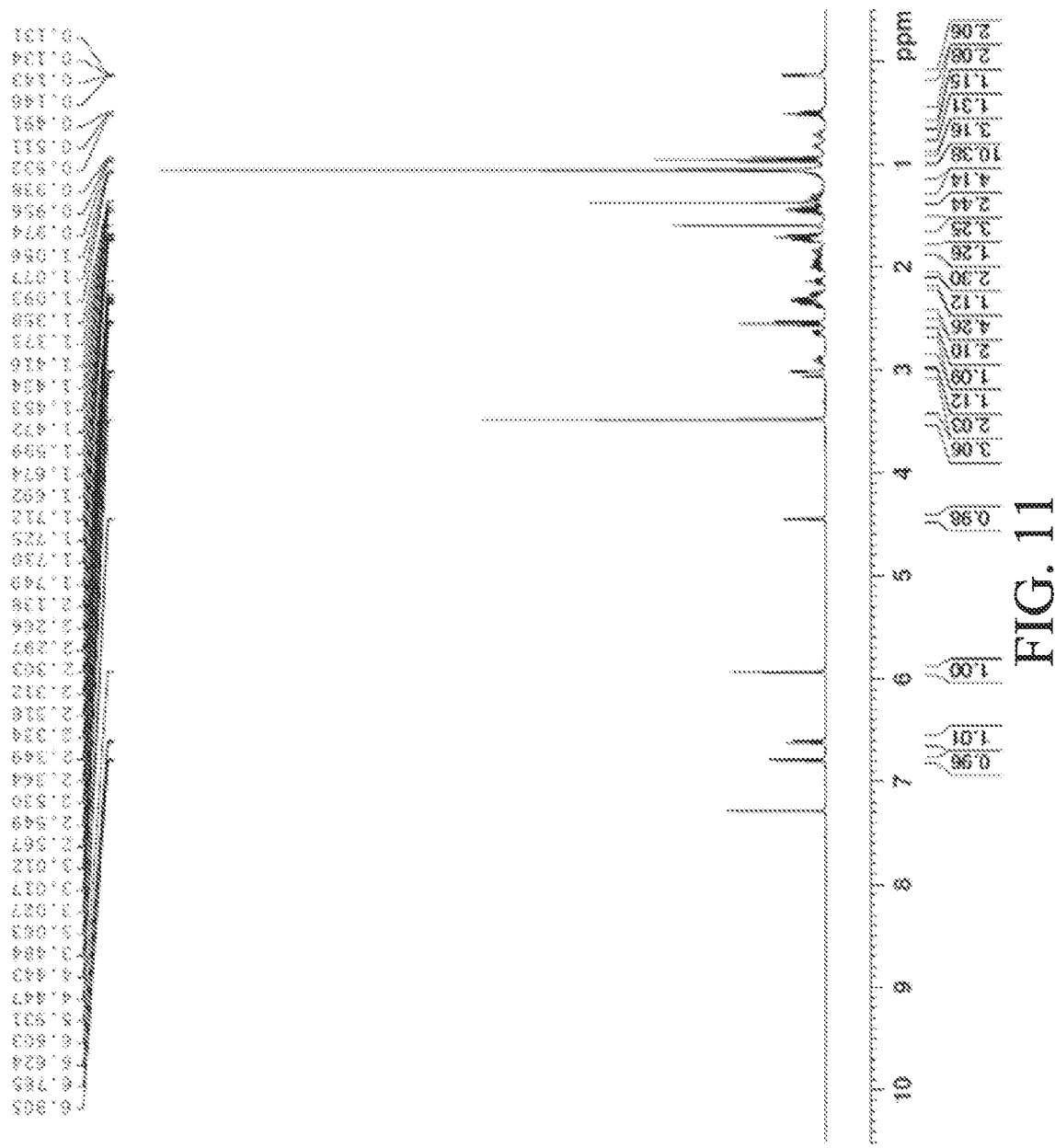
FIG. 11 illustrates the $^1$H NMR spectrum of buprenorphine pentanoate crystal form.
Figure 12:
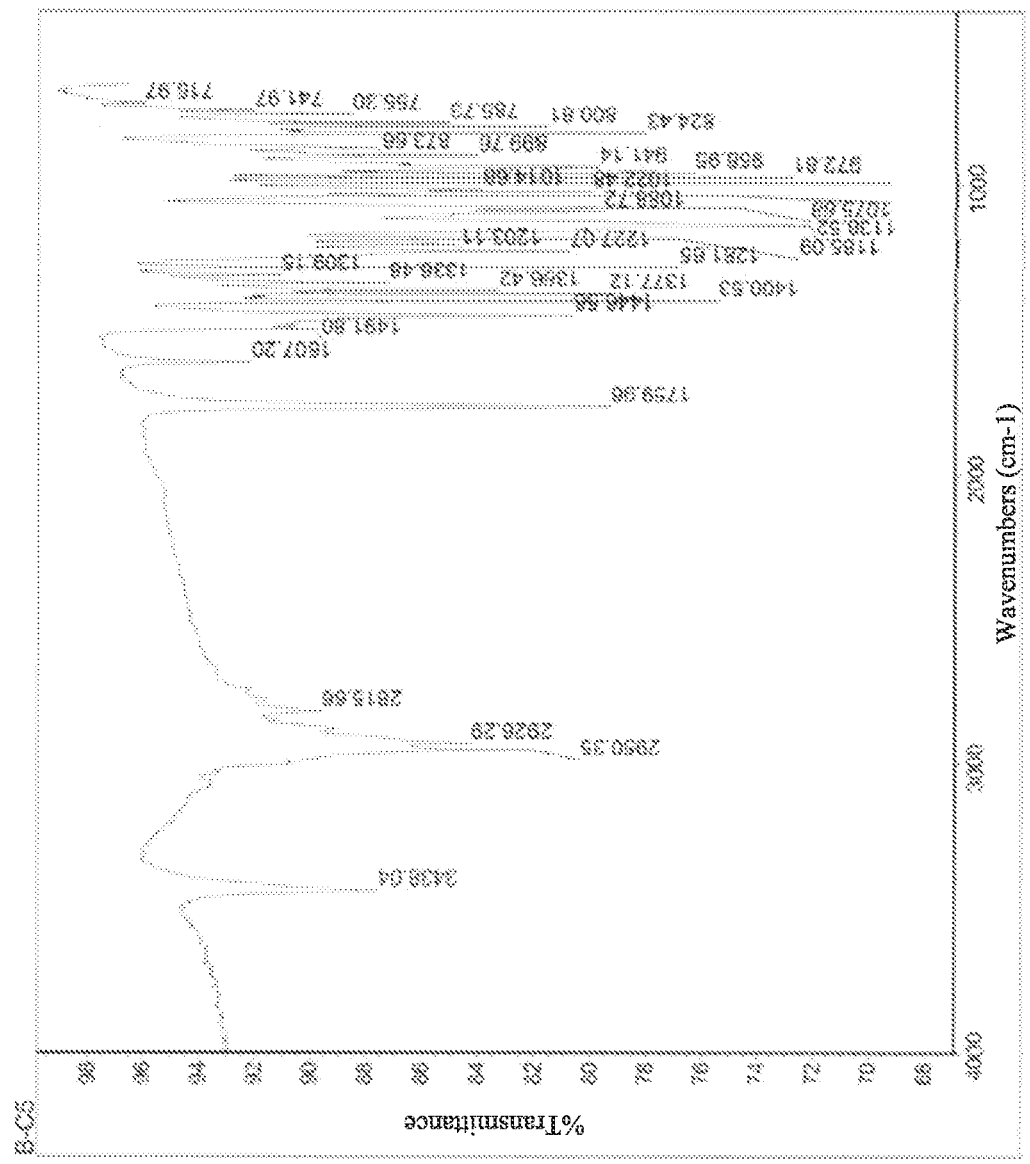
FIG. 12 illustrates the FTIR spectrum of buprenorphine pentanoate crystal form.

The crystal form of buprenorphine pentanoate was characterized by X-ray diffraction pattern (PHILIPS X'PERT Pro, PHILIPS X'PERT Pro MPD) having peaks at 2.33, 5.73, 5.83, 5.98, 6.13, 9.33, 9.43, 9.53, 9.63, 9.98, 10.08, 10.18, 11.83, 11.93, 12.03, 12.53, 12.68, 12.83, 12.98, 13.08, 15.73, 15.88, 16.03, 16.38, 18.28, 18.38, 18.58, 19.28, 19.43, 22.23 degrees 2θ (FIG. 9), and its melting point was determined to be 104.98 to 108.32° C. by means of differential scanning calorimetry, DSC (Mettler-Toledo, TGA/DSC 3+ STARe System) (FIG. 10). The structure of the buprenorphine pentanoate crystal form was identified with Nuclear Magnetic Resonance, NMR (Bruker, Ascend™ 400 MHz) and Fourier Transform Infrared Spectroscopy, FTIR (Thermo, Nicolet-IS10 Mattson Satellite-5000 spectrometer) (FIGS. 11 and 12). Representative $^1$H NMR (400 MHz, CDCl$_3$): 6.79 (d, 1H, J=8.0 Hz), 6.61 (d, 1H, J=8.0 Hz), 5.93 (s, 1H), 4.44 (d, 1H, J=1.6 Hz), 3.48 (s, 3H), 3.04 (m, 2H), 2.91 (m, 1H), 2.64 (dd, 1H, J=4.8, 12.0 Hz), 2.55 (t, 2H, J=7.6 Hz), 2.40-2.20 (m, 4H), 2.14 (t, 1H, 2.07-1.78 (m, 3H), 1.78-1.68 (m, 3H), 1.48-1.28 (m, 6H), 1.15-1.01 (m, 10H), 0.94 (t, 3H, J=7.2 Hz), 0.83 (m, 1H), 0.71 (m, 1H), 0.51 (m, 2H), 0.14 (m, 2H). FTIR absorption band (cm$^{-1}$): 3438, 2950, 2926, 2816, 1760, 1607, 1492, 1447, 1401 (±1 cm$^{-1}$).

Figure 13:
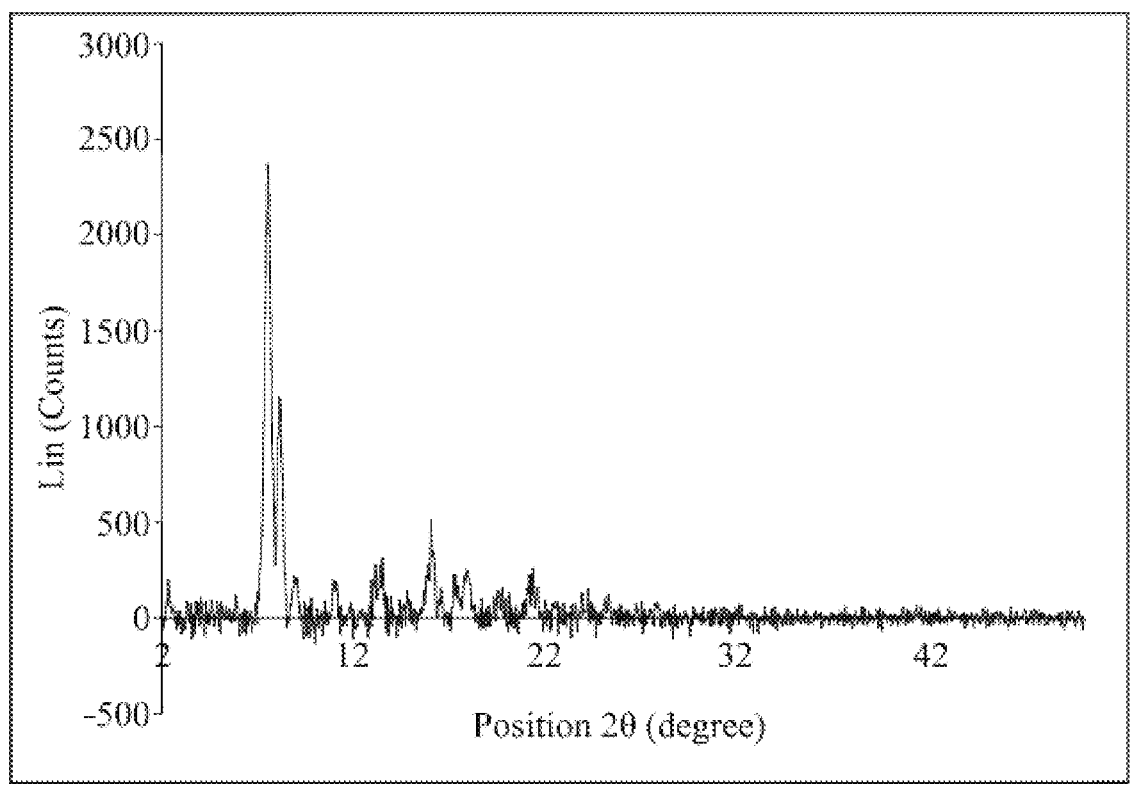
FIG. 13 illustrates the X-ray powder diffraction pattern of buprenorphine hexanoate crystal form.
Figure 14:
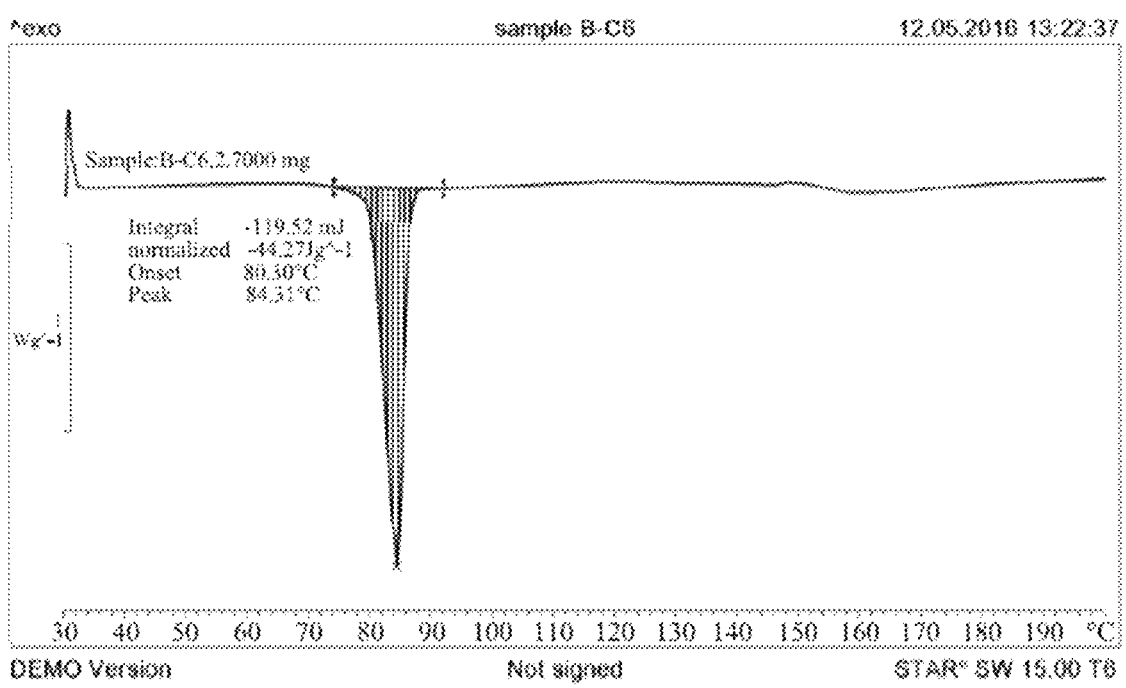
FIG. 14 illustrates the DSC pattern of buprenorphine hexanoate crystal form.
Figure 15:
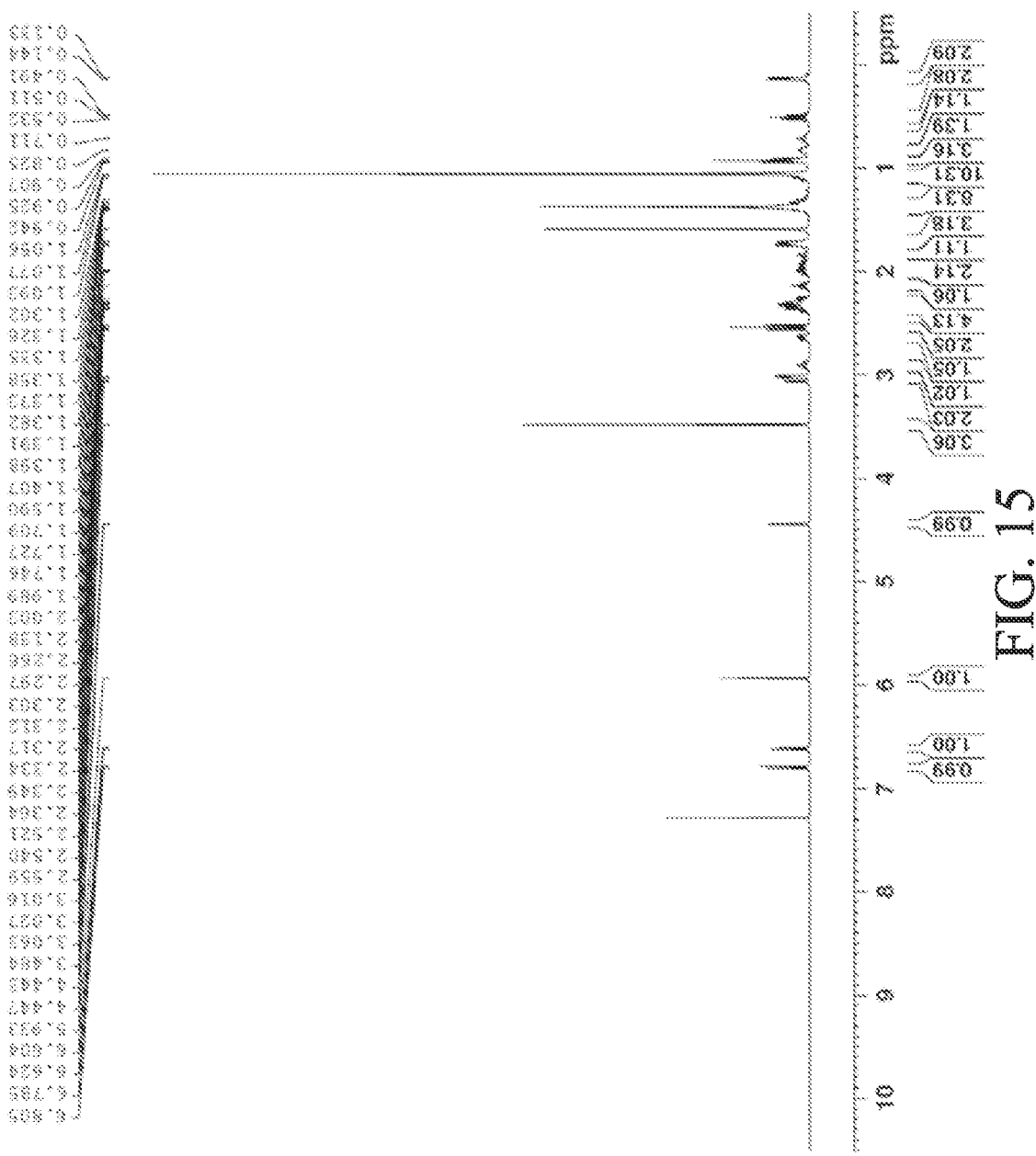
FIG. 15 illustrates the $^1$H NMR spectrum of buprenorphine hexanoate crystal form.
Figure 16:
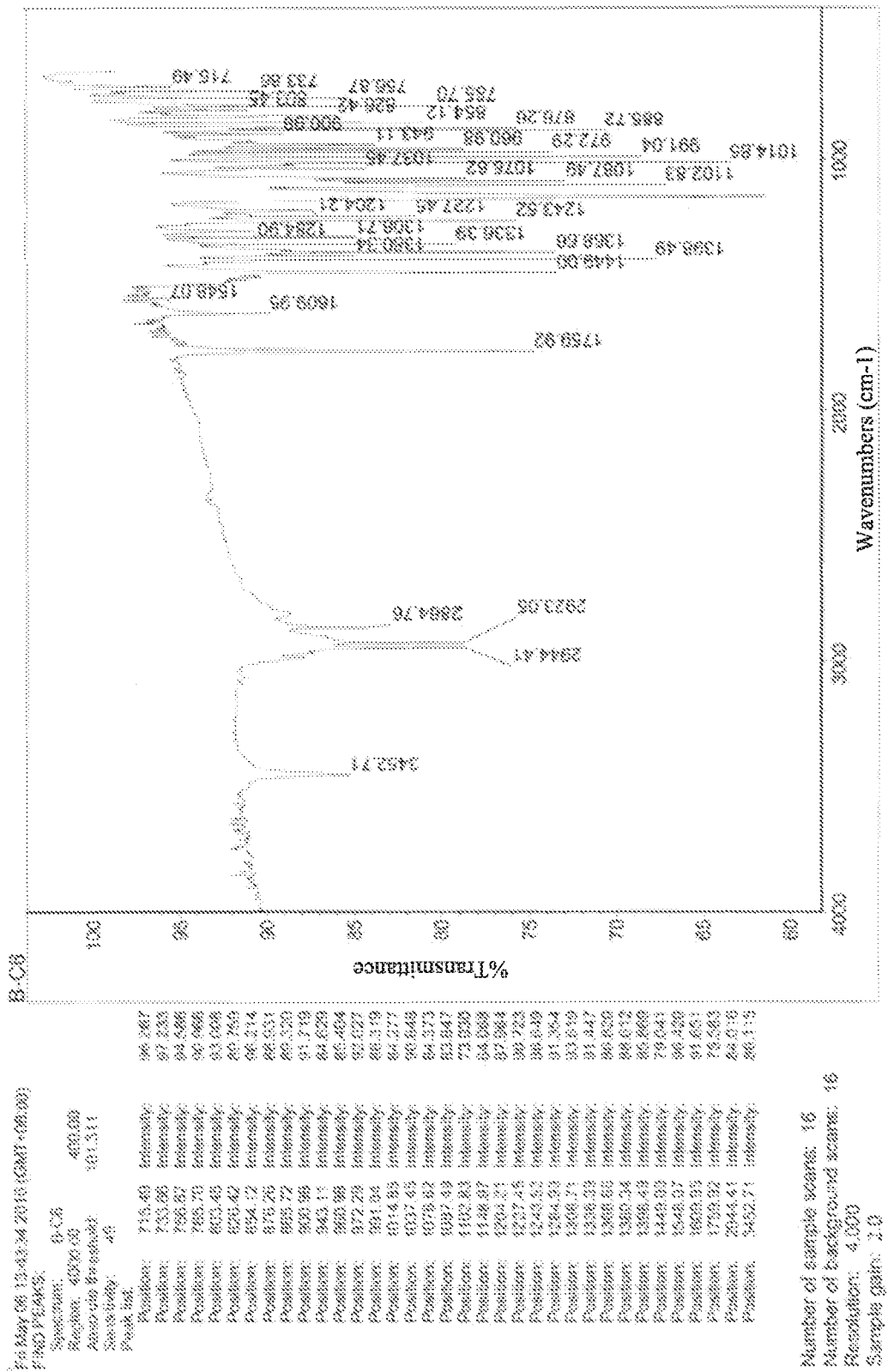
FIG. 16 illustrates the FTIR spectrum of buprenorphine hexanoate crystal form.

The crystal form of buprenorphine hexanoate was characterized by X-ray diffraction pattern (PHILIPS X'PERT Pro, PHILIPS X'PERT Pro MPD) having peaks at 2.33, 7.53, 8.13, 9.05, 10.93, 11.08, 12.93, 13.13, 13.38, 13.48, 15.88, 16.03, 17.18, 17.28, 17.73, 17.93, 21.13, 21.23, 21.33 degrees 2θ (FIG. 13), and its melting point was determined to be 80.30 to 84.31° C. by means of differential scanning calorimetry, DSC (Mettler-Toledo, TGA/DSC 3+ STARe System) (FIG. 14). The structure of the buprenorphine hexanoate crystal form was identified with Nuclear Magnetic Resonance, NMR (Bruker, Ascend™ 400 MHz) and Fourier Transform Infrared Spectroscopy, FTIR (Thermo, Nicolet-IS10 Mattson Satellite-5000 spectrometer) (FIGS. 15 and 16). Representative $^1$H NMR (400 MHz, CDCl$_3$): 6.79 (d, 1H, J=8.0 Hz), 6.61 (d, 1H, J=8.0 Hz), 5.93 (s, 1H), 4.44 (d, 1H, J=1.6 Hz), 3.48 (s, 3H), 3.04 (m, 2H), 2.91 (m, 1H), 2.64 (dd, 1H, J=4.8, 12.0 Hz), 2.54 (t, 2H, J=7.6 Hz), 2.45-2.20 (m, 4H), 2.14 (t, 1H), 2.08-1.65 (m, 6H), 1.42-1.30 (m, 8H), 1.16-1.02 (m, 10H), 0.93 (t, 3H, J=6.8 Hz), 0.83 (m, 1H), 0.71 (m, 1H), 0.51 (m, 2H), 0.14 (m, 2H). FTIR absorption band (cm$^{-1}$): 3453, 2944, 2923, 2865, 1760, 1610, 1449, 1398 (±1 cm$^{-1}$).

Figure 17:
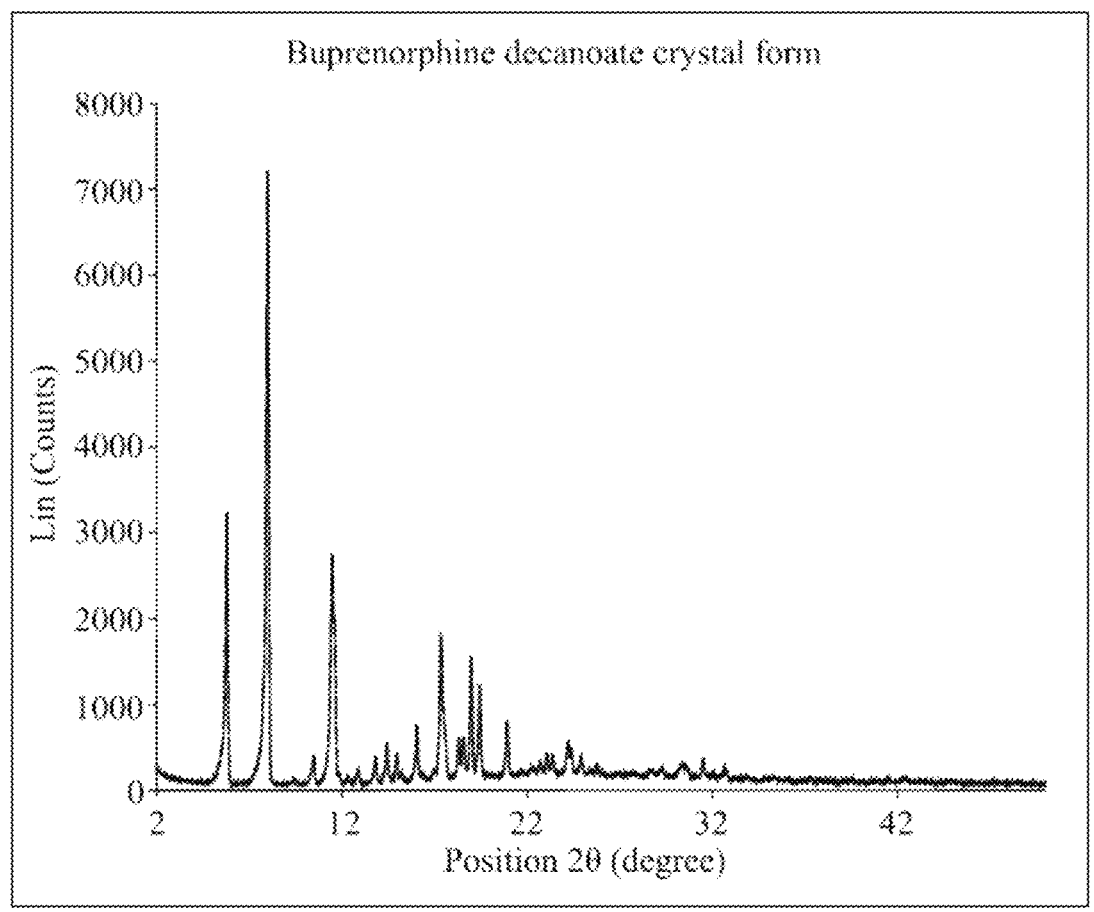
FIG. 17 illustrates the X-ray powder diffraction pattern of buprenorphine decanoate crystal form.
Figure 18:
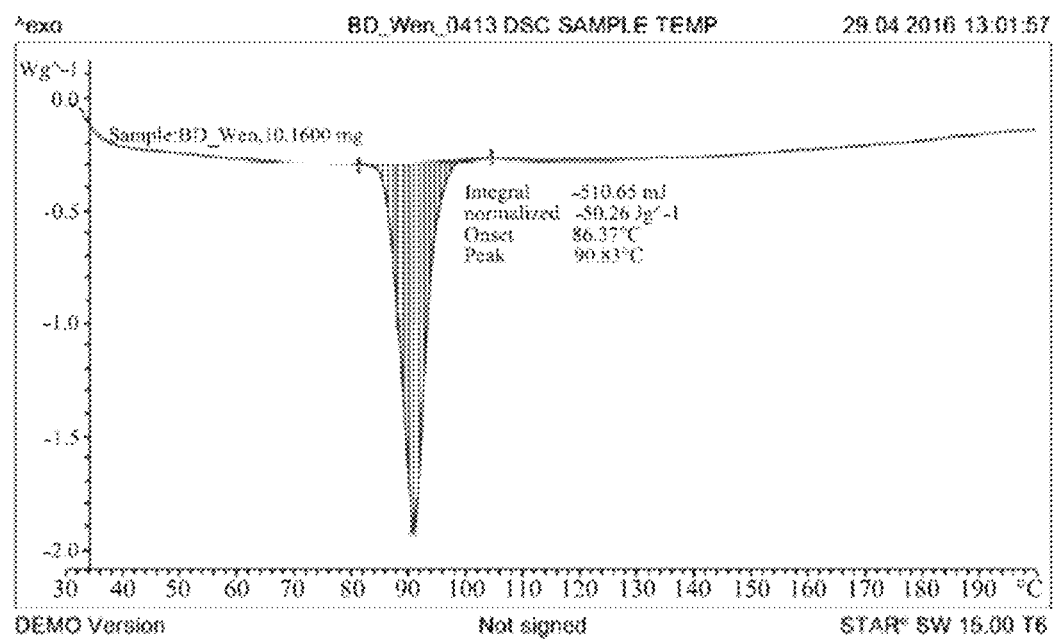
FIG. 18 illustrates the DSC pattern of buprenorphine decanoate crystal form.
Figure 19:
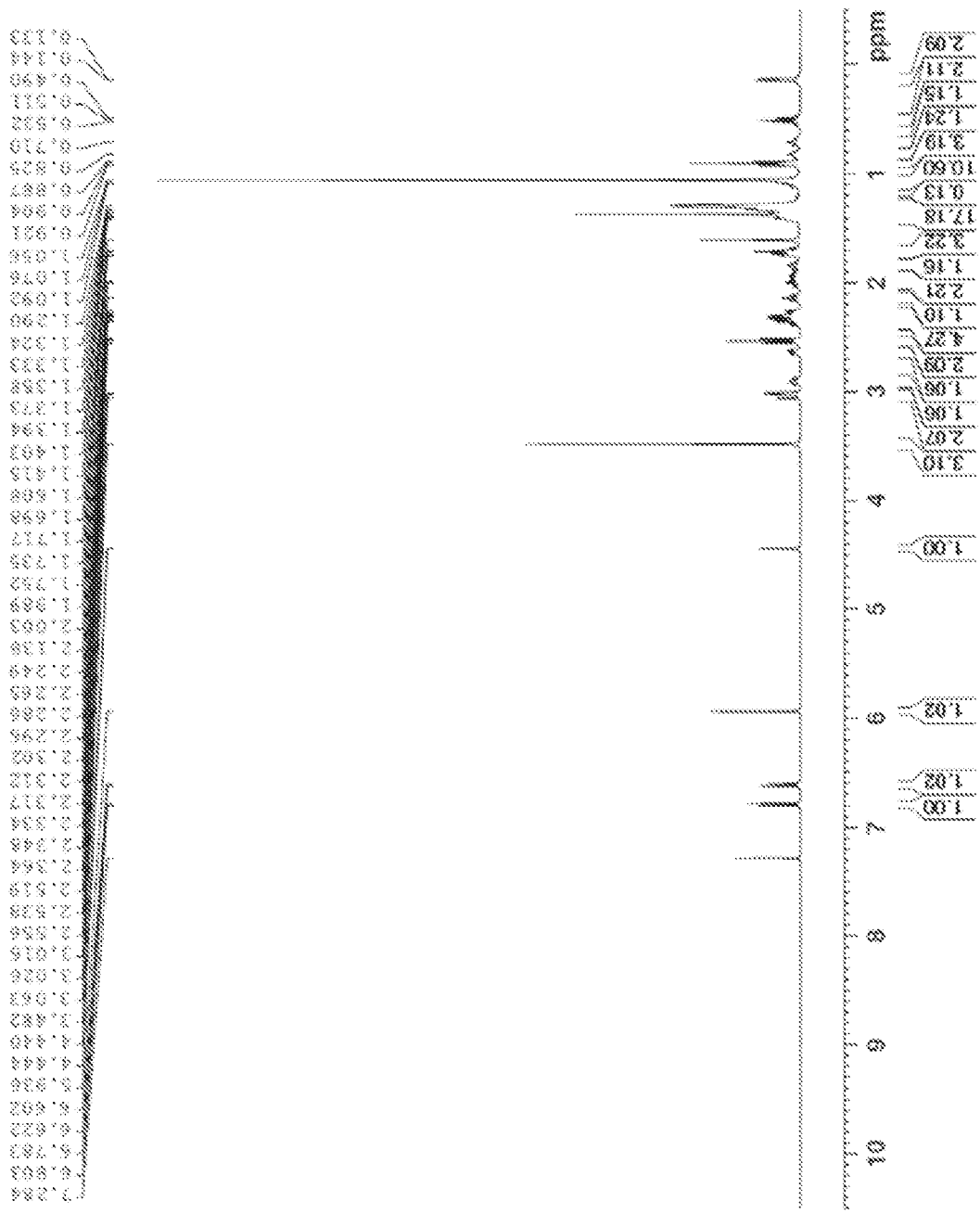
FIG. 19 illustrates the $^1$H NMR spectrum of buprenorphine decanoate crystal form.
Figure 20:
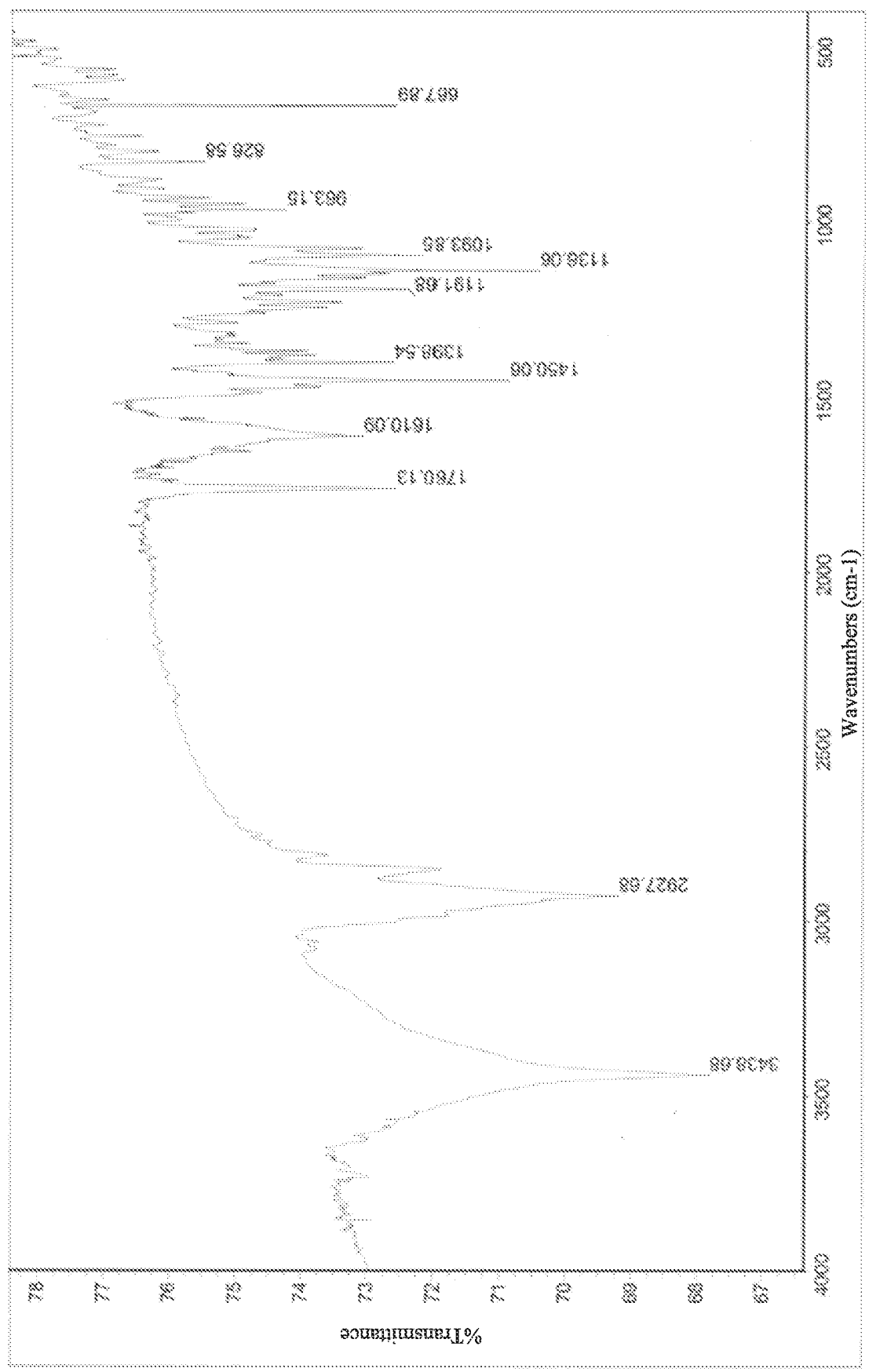
FIG. 20 illustrates the FTIR spectrum of buprenorphine decanoate crystal form.

The crystal form of buprenorphine decanoate was characterized with X-ray diffraction pattern (Bruker, D8 DISCOVER SSS Multipurpose Thin-film X-ray Diffractometer), which shows peaks at 5.80, 8.00, 10.50, 11.50, 11.60, 13.82, 14.44, 14.96, 16.06, 17.34, 18.32, 18.58, 18.98, 19.44, 20.92, 23.06, 23.40, 24.22, 24.38, 24.92 degrees 2θ (FIG. 17), and its melting point of the crystal product was determined to be 86.37° C. by means of differential scanning calorimetry, DSC (Mettler-Toledo, TGA/DSC 3+ STARe System) (FIG. 18). The structure of buprenorphine decanoate was identified with Nuclear Magnetic Resonance, NMR (Bruker, Ascend™ 400 MHz) and Fourier Transform Infrared Spectroscopy, FTIR (Thermo, Nicolet-IS10 Mattson Satellite-5000 spectrometer). (FIGS. 19 and 20). Representative $^1$H NMR (400 MHz, CDCl$_3$): 6.79 (d, 1H, J=8.0 Hz), 6.61 (d, 1H, J=8.0 Hz), 5.94 (s, 1H), 4.44 (d, 1H, J=1.6 Hz), 3.48 (s, 3H), 3.04 (m, 2H), 2.91 (m, 1H), 2.64 (dd, 1H, J=5.2, 12.0 Hz), 2.54 (t, 2H, J=7.2 Hz), 2.40-2.25 (m, 4H), 2.14 (t, 1H, J=9.6 Hz), 2.03-1.90 (m, 2H), 1.87-1.80 (m, 1H), 1.75-1.68 (m, 3H), 1.42-1.29 (m, 17H), 1.12-1.06 (m, 9H), 0.94 (t, 3H, J=6.8 Hz), 0.83 (m, 1H), 0.71 (m, 1H), 0.51 (m, 2H), 0.14 (m, 2H). FTIR absorption band (cm$^{-1}$): 3439, 2928, 1760, 1610, 1450, 1399, 1192, 1136, 1094, 963, 827, and 668 (±1 cm$^{-1}$).

Figure 21:
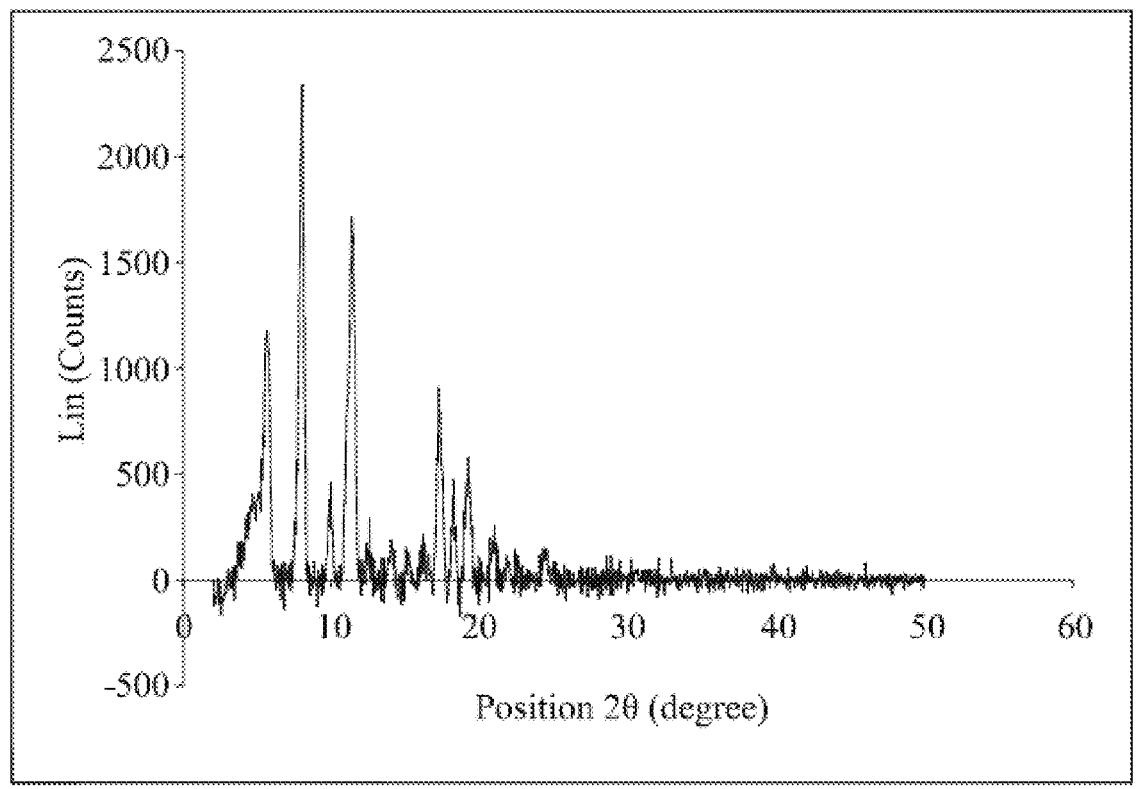
FIG. 21 illustrates the X-ray powder diffraction pattern of buprenorphine dodecanoate crystal form.
Figure 22:
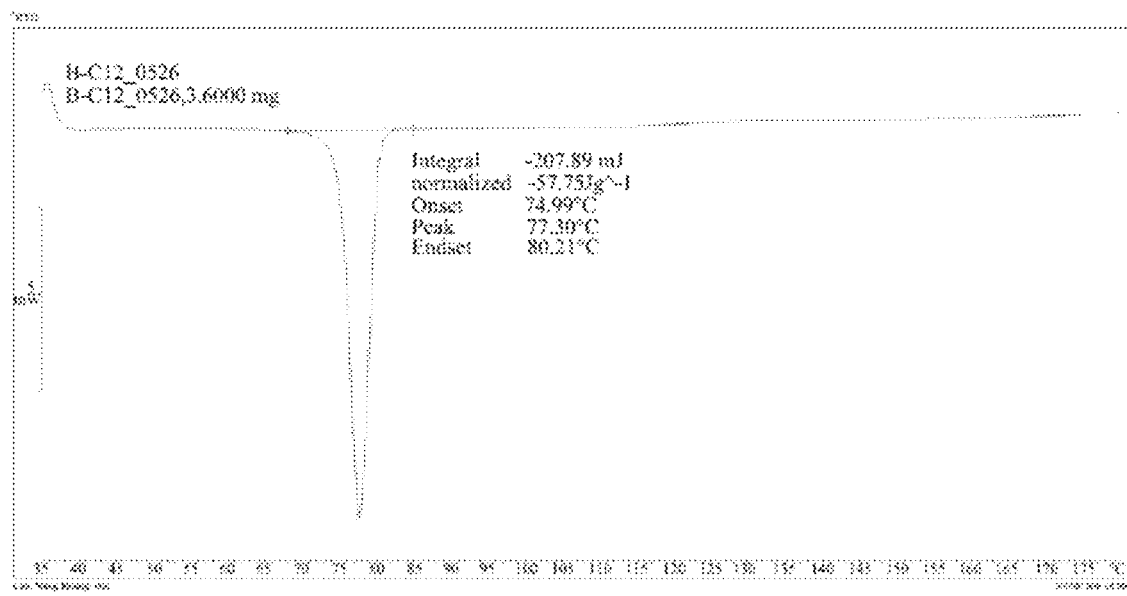
FIG. 22 illustrates the DSC pattern of buprenorphine dodecanoate crystal form.
Figure 23:
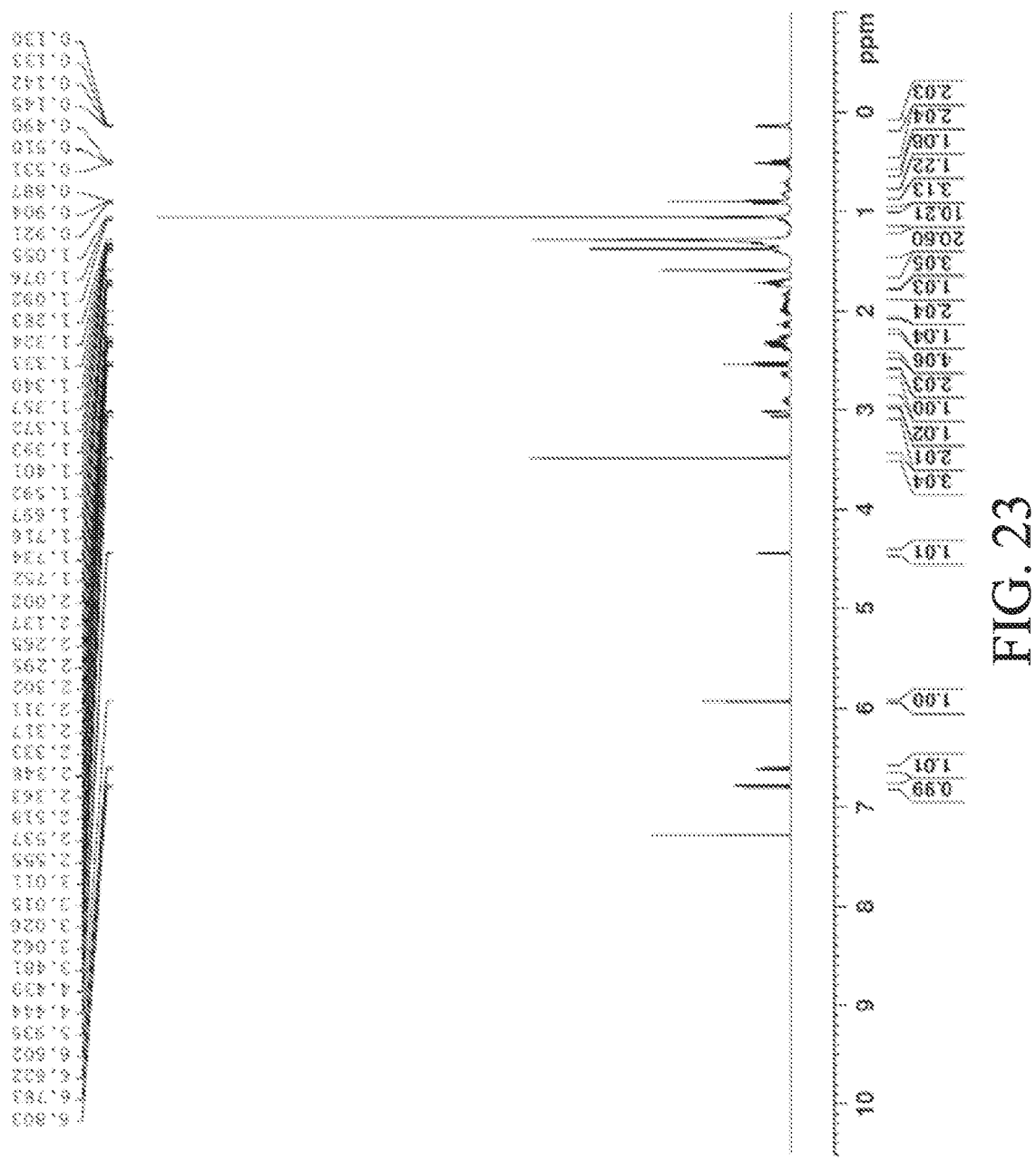
FIG. 23 illustrates the $^1$H NMR spectrum of buprenorphine dodecanoate crystal form.
Figure 24:
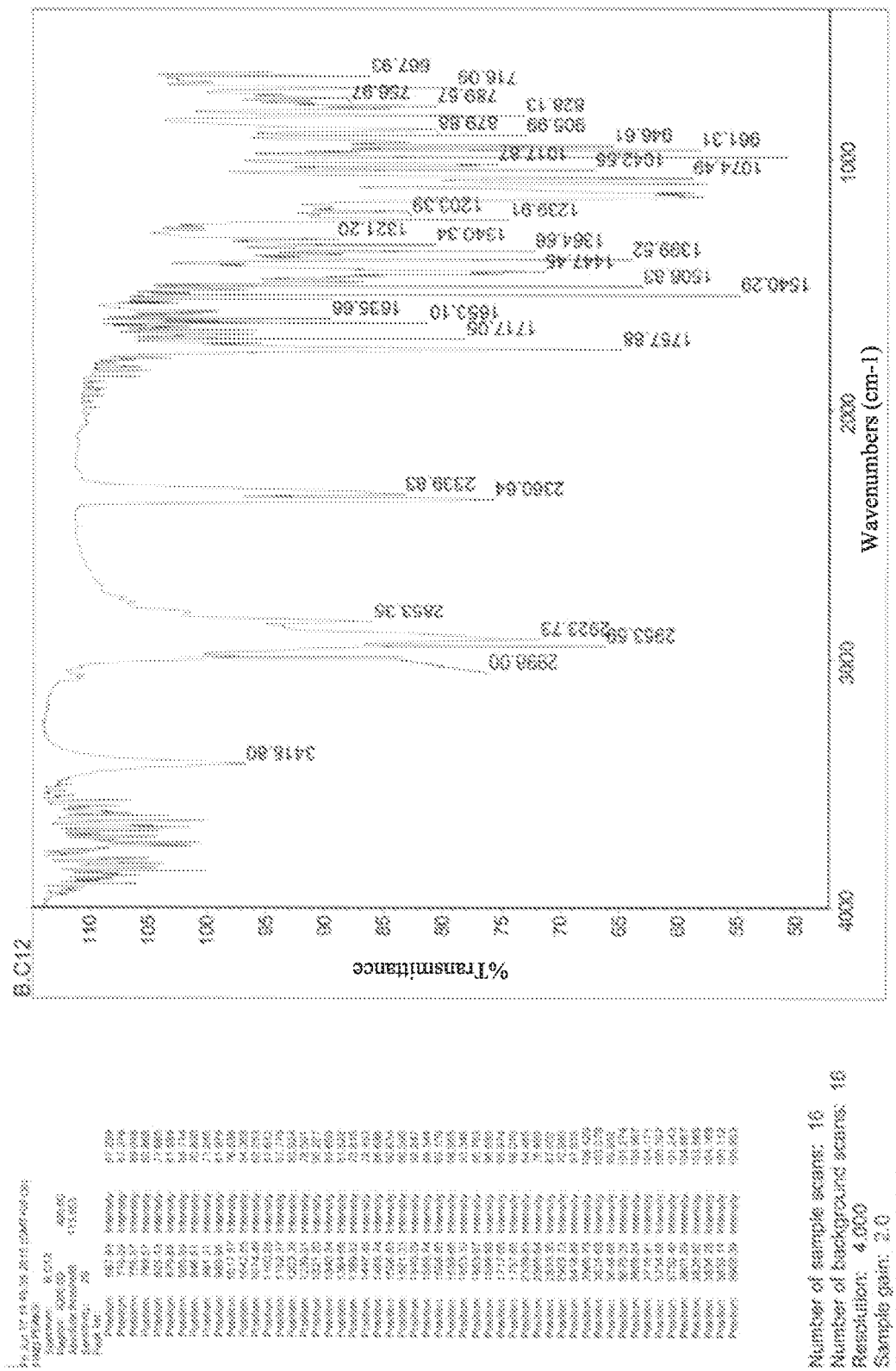
FIG. 24 illustrates the FTIR spectrum of buprenorphine dodecanoate crystal form.
Figure 25:
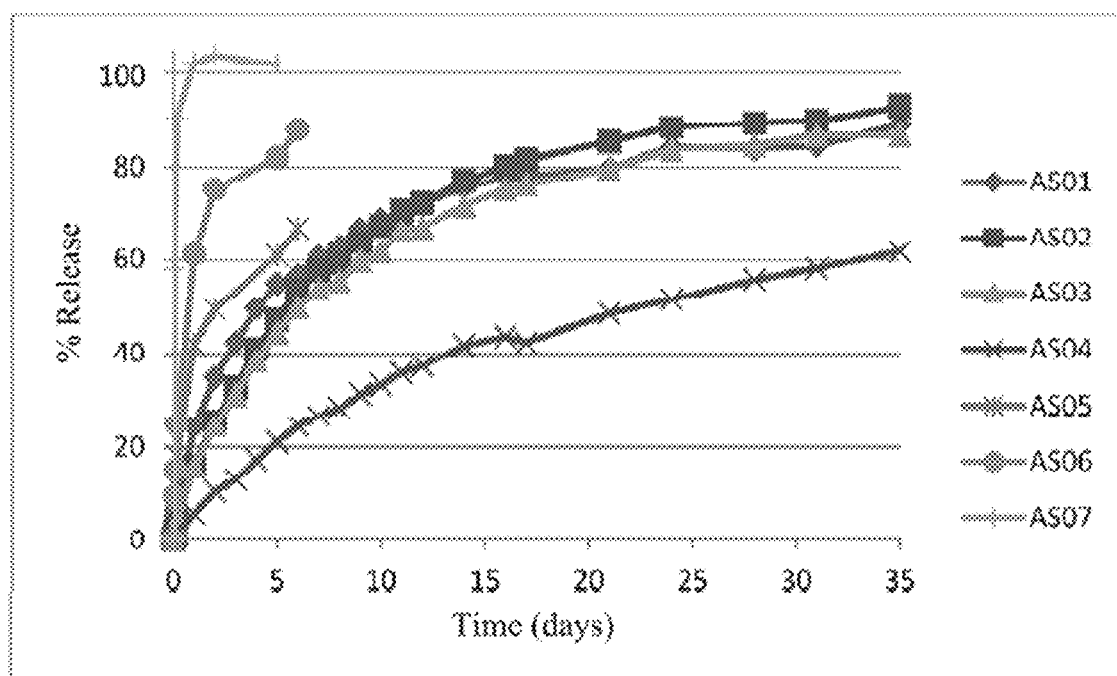
FIG. 25 illustrates the in vitro dissolution % release of AS01-07.
Figure 26:
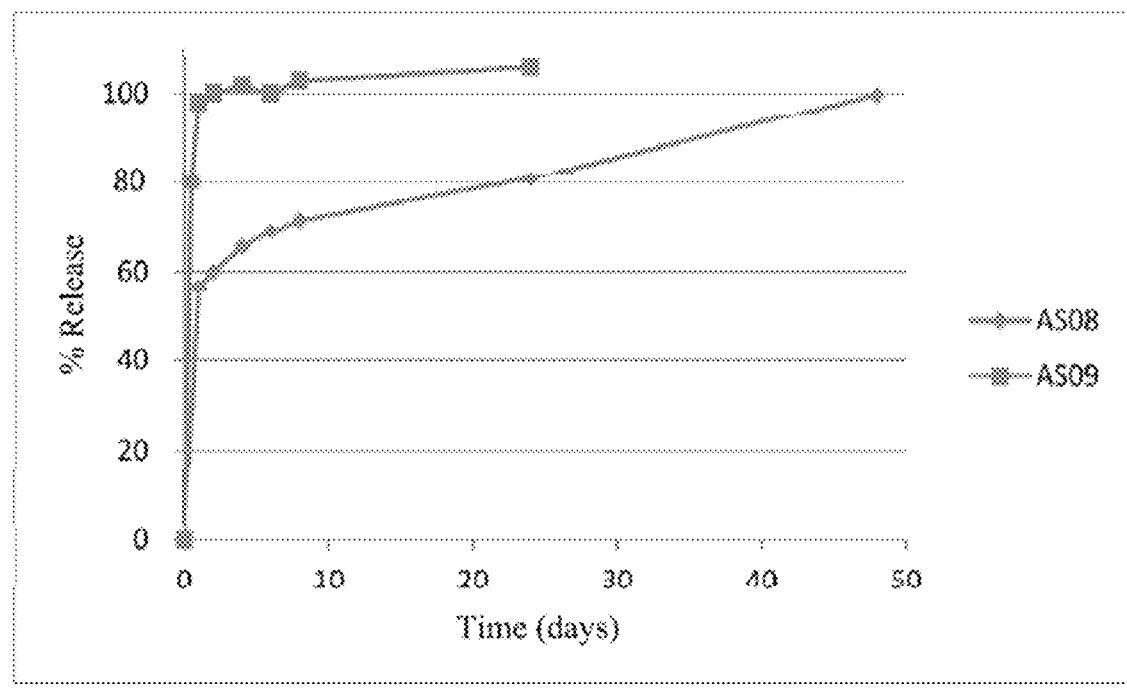
FIG. 26 illustrates the in vitro dissolution % release of AS08-09.
Figure 27:
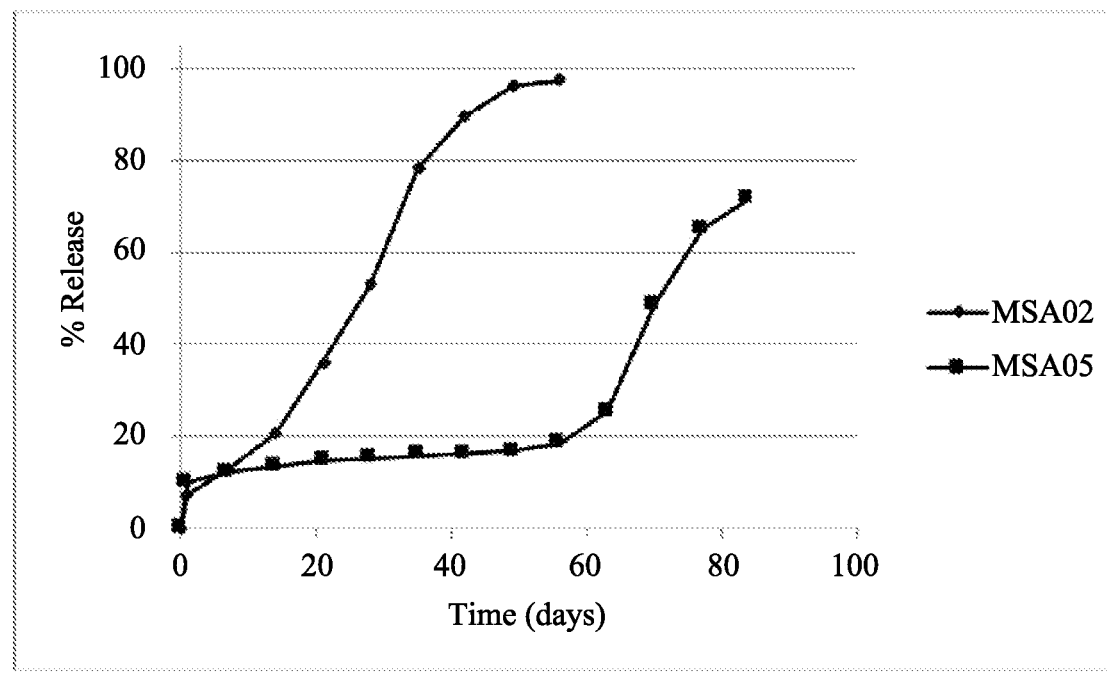
FIG. 27 illustrates the in vitro dissolution % release of MSA02 and MSA05.
Figure 28:
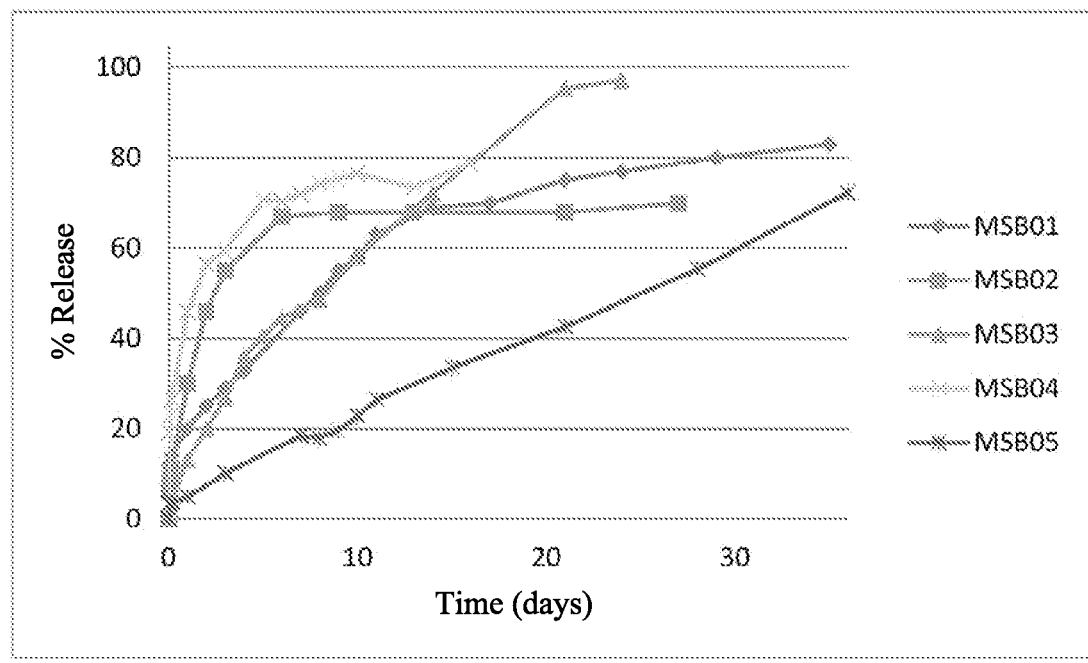
FIG. 28 illustrates the in vitro dissolution % release of MSB01-05.
Figure 29:
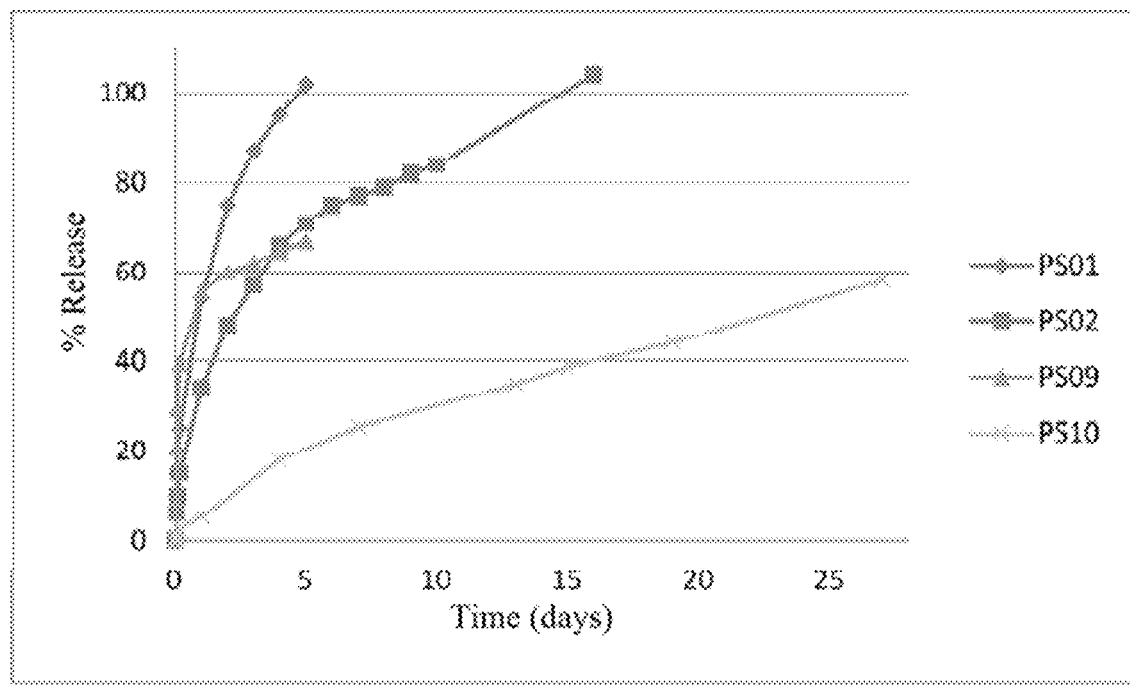
FIG. 29 illustrates the in vitro dissolution % release of PS01, PS02, PS09, and PS10.
Figure 30:
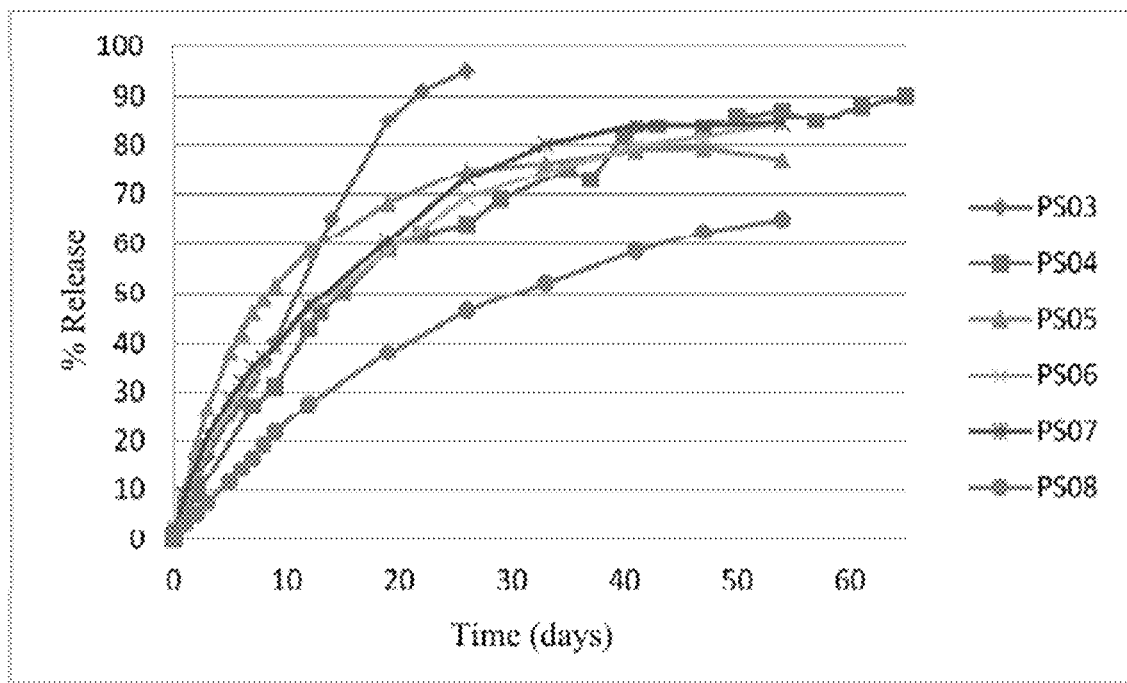
FIG. 30 illustrates the in vitro dissolution % release of PS03-08.
Figure 31:
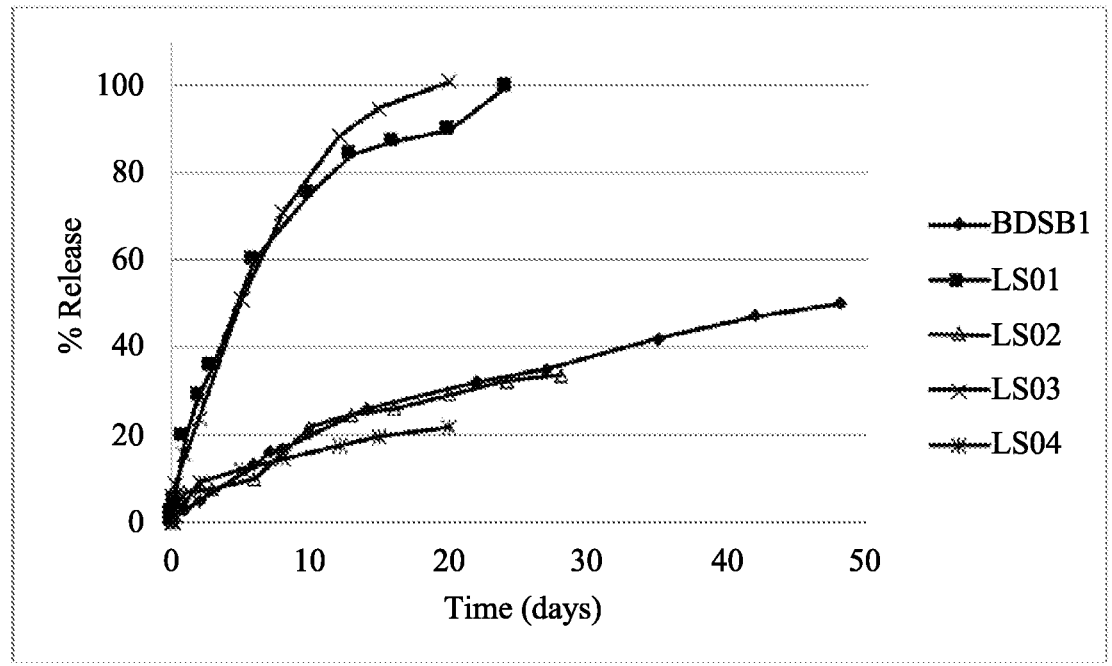
FIG. 31 illustrates the in vitro dissolution % release of BDSB1 and LS01-04.

The crystal form of buprenorphine dodecanoate was characterized by X-ray diffraction pattern (PHILIPS X'PERT Pro, PHILIPS X'PERT Pro MPD) having peaks at 5.68, 8.03, 9.88, 9.98, 10.93, 11.38, 11.48, 17.13, 17.23, 17.33, 18.18, 18.28, 18.38, 18.93, 19.13, 19.23, 19.53, 21.03 degrees 2θ(FIG. 21) and its melting point was determined to be 74.99 to 77.30° C. by means of differential scanning calorimetry, DSC (Mettler-Toledo, TGA/DSC 3+ STARe System) (FIG. 22). The structure of the buprenorphine dodecanoate crystal form was identified with Nuclear Magnetic Resonance, NMR (Bruker, Ascend™ 400 MHz) and Fourier Transform Infrared Spectroscopy, FTIR (Thermo, Nicolet-IS10 Mattson Satellite-5000 spectrometer) (FIGS. 23 and 24). Representative $^1$H NMR (400 MHz, CDCl$_3$): 6.79 (d, 1H, J=8.0 Hz), 6.61 (d, 1H, J=8.0 Hz), 5.94 (s, 1H), 4.44 (d, 1H, J=2.0 Hz), 3.48 (s, 3H), 3.10-3.00 (m, 2H), 2.97-2.87 (m, 1H), 2.64 (dd, 1H, J=4.8, 12.0 Hz), 2.54 (t, 2H, J=7.6 Hz), 2.42-2.22 (m, 4H), 2.14 (t, 1H, J=9.6 Hz), 2.07-1.78 (m, 3H), 1.77-1.66 (m, 3H), 1.46-1.22 (m, 20H), 1.14-1.01 (m, 10H), 0.90 (t, 3H, J=6.8 Hz), 0.87-0.78 (m, 1H), 0.77-0.65 (m, 1H), 0.58-0.45 (m, 2H), 0.19-0.08 (m, 2H). FTIR absorption band (cm$^{-1}$): 3453, 2944, 2923, 2865, 1760, 1610, 1449, 1398 (±1 cm$^{-1}$).

The above examples show limited numbers of ester derivatives of the disclosure. One skilled in the art would appreciate that other similar ester derivatives may be prepared in similar manners.

EXAMPLE 3

Solubility of Buprenorphine Derivatives and Salt Form Thereof in Dissolution Medium Excess amount of compounds, including buprenorphine free base, buprenorphine derivatives, or salt form thereof were weighed into a glass tube containing 5 mL dissolution medium. The medium was the same as in previous examples. The tube was then sealed and placed into a reciprocal shaker at the rate of 60 rpm in a 55° C. water bath. The solution was filtered with 0.45 μm Nylon filter. Afterwards, the filtrate was further diluted with acetonitrile. The content of each compound was measured with the HPLC method.

TABLE 3

Solubility of buprenorphine derivatives

| Compound | Solubility (mg/mL) |
| --- | --- |
| Buprenorphine free base | 1.176 |
| Buprenorphine acetate (crystal form) | 0.697 |
| Buprenorphine pentanoate (crystal form) | 0.498 |
| Buprenorphine hexanoate (crystal form) | 0.670 |
| Buprenorphine pivalate (crystal form) | 0.160 |
| Buprenorphine decanoate (crystal form) | 0.112 |
| Buprenorphine dodecaonate (crystal form) | 0.269 |
| Buprenorphine palmitate | 0.027 |
| Buprenorphine stearate | 0.020 |

TABLE 4

Solubility of salt forms of buprenorphine derivatives

| Compound | Solubility (mg/mL) |
| --- | --- |
| Buprenorphine-pamoic acid salt | 2.095 |
| Buprenorphine acetate-citric acid salt | 1.377 |
| Buprenorphine acetate-maleic acid salt | 1.481 |
| Buprenorphine acetate-hydrochloride salt | 1.716 |
| Buprenorphine acetate-pamoic acid salt | 1.546 |
| Buprenorphine decanoate-citric acid salt | 2.696 |
| Burpenorphine decaonate-L-tartaric acid salt | 1.507 |
| Buprenorphine stearate-citric acid salt | 2.452 |
| Buprenorphine stearate-L-tartaric acid salt | 3.504 |

Table 3 shows that the solubilities of the buprenorphine derivatives (in crystal form) were less than their parent compound (buprenorphine free base). The solubility of buprenorphine decanoate crystal form was nearly 10 times poorer than that of the parent compound. After preparation of the salt forms, the solubilities of salt forms of buprenorphine derivatives were found to be superior to their free base and parent compound (Table 4).

EXAMPLE 4

Preparation of Aqueous Suspension of Buprenorphine Derivatives

Weighed known amount of 3-acyl-buprenorphine derivative and suspended it with diluent, which was composed of PEG4000 (30 mg/mL) and Tween 20 (3 to 6 mg/mL) in PBS buffer. Mixed the formulation by sonicating and shaking. The formulations were further milled. The composition and process were listed in Table 5. The particle size distribution results were shown in Table 6.

TABLE 5

Composition, milling process and administration route of buprenorphine derivatives aqueous suspension

| Code | Buprenorphine derivatives | Milling Process | Administration route |
|---|---|---|---|
| AS01 | Buprenorphine decanoate, 10% w/v | Agate mortar | IM |
| AS02 | Buprenorphine decanoate, 10% w/v | — | IM |
| AS03 | Buprenorphine decanoate, 10% w/v | — | SC |
| AS04 | Buprenorphine decanoate, 10% w/v | — | IM |
| AS05 | Buprenorphine decanoate, 20% w/v | Bead milling, 6 mm Iron beads | SC |
| AS06 | Buprenorphine decanoate, 20% w/v | Bead milling, 0.50 mm Zirconia Grinding Media | SC |
| AS07 | Buprenorphine hexanoate, 10% w/v | Bead milling, 2 mm glass beads | SC |
| AS08 | Buprenorphine hexanoate, 20% w/v | Bead milling, 0.50 mm Zirconia Grinding Media | SC |
| AS09 | Buprenorphine hexanoate, 15% w/v | High pressure homogenizers (6000 rpm, 20000 psi) | — |
| AS10 | Buprenorphine hexanoate, 30% w/v | Bead milling, 0.50 mm Zirconia Grinding Media | — |

TABLE 6

Particle size distributions of aqueous suspension of buprenorphine derivatives

| Formulation | Volume Statistics | | | |
|---|---|---|---|---|
| | d10 (µm) | d50 (µm) | d90 (µm) | Specific Surface Area (cm²/g) |
| AS01 | 2.15 | 17.07 | 62.33 | 10319 |
| AS02/AS03 | 3.22 | 15.68 | 44.43 | 8816 |
| AS08 | 8.90 | 11.33 | 36.83 | 4521 |
| AS09 | 1.58 | 4.99 | 14.60 | 18183 |

EXAMPLE 5

Preparation of Microspheres

Method A

The process of microsphere preparation in Method A was carried out by double emulsion. A known amount of poly(lactide-co-glycolide) and active pharmaceutical ingredient were weighed into a glass vial. Dichloromethane (3 mL) was used to dissolve the mixture. Polyvinyl alcohol aqueous solution (1%, 6 mL) was added thereto. The mixture was suspended using a homogenizer at the rate of 5000 rpm for 5 minutes in an ice bath. The homogenous suspension was then dropped into a beaker containing polyvinyl alcohol aqueous solution (1%, 1000 mL) with stirring (800 rpm) at 40° C. under a heating condition. After 3 hours, the microparticles were collected with centrifuge and washed with dd-water several times sequentially. The residual water in microparticles was removed by freeze drying. The formulation compositions are listed in Table 7 below.

TABLE 7

Composition of microspheres (Method A)

| Formulation | API | | PLGA type | E.E. (%) | Particle size (mean, µm) |
|---|---|---|---|---|---|
| | Compound | wt % | LA/GA ratio | | |
| MSA01 | Buprenorphine decanoate | 40% | 75/25 (iv 0.21, ester capped) | 100.2 ± 1.5 | 24.6 ± 7.7 |
| MSA02 | Buprenorphine decanoate citric acid salt | 40% | 50/50 (iv 0.30, acid terminated) | 108.9 ± 5.1 | 24.6 ± 7.9 |
| MSA03 | Buprenorphine decanoate citric acid salt | 50% | 50/50 (iv 0.21, acid terminated) | 115.9 ± 2.9 | 8.4 ± 6.3 |
| MSA04 | Buprenorphine decanoate citric acid salt | 40% | 50/50 (iv 0.21, acid terminated) | 115.6 ± 1.7 | 5.6 ± 6.2 |
| MSA05 | Buprenorphine decanoate citric acid salt | 40% | 75/25 (iv 0.21, ester capped) | 111.0 ± 3.6 | 20.8 ± 7.2 |

Method B

Method B was conducted using a T-shaped loop (Western Analytical, Tee Asy Tefzel 1/16" 0.020" thru). The terminal inlet was inserted with one set of syringe and needle (Hamilton 81520 5 mL, Model 1005 TLL and Hamilton Metal Hub N726S NDL 6/PK (26S/2"/3)) as a dispersing phase part. One of the lateral inlets was connected with a pump with a tubing as a continuous phase part.

The microspheres were prepared using a continuous emulsification/solvent extraction procedure. The dispersing phase was filled into a syringe with an API-containing polymer solution, which was composed of PLGA and dichloromethane. The flow rate of the dispersing phase was controlled by an infusion syringe pump (KDS 100, KD Scientific) at a rate of 0.3 mL/min. At the same time, the continuous phase containing 1% polyvinyl alcohol aqueous solution was pumped at a rate of 2 mL/min. The outlet was connected to a beaker containing 1% polyvinyl alcohol aqueous solution through a tubing. The quenching process was carried out at ambient or heating condition. The microspheres were filtered with 0.45 µm membrane and washed with dd-water several times. Thereafter, the microspheres were dried in vacuum at ambient temperature. The formulation compositions are listed in Table 8.

TABLE 8

| | Composition of microsphere (Method B) | | | | | |
|---|---|---|---|---|---|---|
| | API | | PLGA type | | | Particle size |
| Formulation | Compound | wt % | LA/GA | I.V. (dL/g) | E.E. | (mean, μm) |
| MSB0 | Buprenorphine decanoate | 40% | 75/25 | 0.7 | 101.6% | NA |
| MSB02 | Buprenorphine hexanoate | 40% | 75/25 | 0.2 | 108.7% | NA |
| MSB03 | Buprenorphine decanoate citric acid salt | 40% | 75/25 | 0.2 | 101.6 | 57.4 |
| MSB04 | Buprenorphine acetate | 40% | 75/25 | 0.2 | 101.2 | 30 |
| MSB05 | Buprenorphine dodecanoate | 40% | 75/25 | 0.2 | 106.8 | 25 |

EXAMPLE 6

Preparation of PLGA-Based Formulation

The buprenorphine derivatives, poly(lactide-co-glycolide), and a biocompatible solvent were added into a glass vial. The mixture was placed into a 50° C. water bath with constant stirring until all the ingredients were dissolved. The mixture was removed from water bath, and the solution was generated at ambient temperature with stirring simultaneously. The compositions of the PLGA-based formulations are listed in Table 9 below.

TABLE 9

| | Compositions of PLGA-based formulations | | |
|---|---|---|---|
| Formulation | Buprenorphine derivatives, wt % | PLGA type, wt % | Solvent, wt % |
| PS01 | Buprenorphine decanoate, 20% | 50/50 (17 kD, ester capped), 20% | EtOAc, 60% |
| PS02 | Buprenorphine decanoate, 20% | 75/25 (95 kD, ester capped), 20% | EtOAc, 60% |
| PS03 | Buprenorphine decanoate, 30% | 75/25 (17 kD, ester capped), 10% | NMP, 60% |
| PS04 | Buprenorphine decanoate, 30% | 75/25 (95 kD, ester capped), 10% | NMP, 60% |
| PS05 | Buprenorphine decanoate, 30% | Polylactide, (17 kD, ester capped), 10% | NMP, 60% |
| PS06 | Buprenorphine decanoate, 30% | Polylactide, (17 kD, acid terminated), 10% | NMP, 60% |
| PS07 | Buprenorphine decanoate, 30% | 50/50 (17 kD, ester capped), 10% | NMP, 60% |
| PS08 | Buprenorphine decanoate, 30% | 50/50 (44 kD, ester capped), 10% | NMP, 60% |
| PS09 | Buprenorphine decanoate citric acid salt, 20% | 75/25 (17 kD, ester capped), 20% | EtOAc, 60% |
| PS10 | Buprenorphine hexanoate, 40% | 75/25 (17 kD, ester capped), 10% | EtOAc, 50% |

EXAMPLE 7

Preparation of Lipid-Based Formulations

The lipid-based formulations were prepared by mixing buprenorphine derivatives, lecithin, diolein, and a biocompatible solvent. The compositions of the lipid-based formulations are listed in Table 10 below.

TABLE 10

| | Compositions of lipid-based formulations | | | |
|---|---|---|---|---|
| | Composition w/w % | | | |
| Formulation | Buprenorphine derivatives | Lecithin | Diolein | Solvent |
| LS01 | Buprenorphine hexanoate, 35% | 17.5% | 17.5% | N-Methyl-2-Pyrrolidone, 30% |
| LS02 | Buprenorphine hexanoate, 35% | 17.5% | 17.5% | Benzyl benzoate, 30% |
| LS03 | Buprenorphine decanoate, 25% | 20% | 20% | N-Methyl-2-Pyrrolidone, 35% |
| LS04 | Buprenorphine decanoate, 25% | 20% | 20% | Benzyl benzoate, 35% |

EXAMPLE 8

Preparation of SAIB-Based Liquid Formulations

Buprenorphine decanoate (203.1 mg, 1.0 eq.) was dissolved in ethanol (2 mL). Sodium dodecyl sulfate (SDS) was dissolved in distilled deionized water (20 mL). The buprenorphine decanoate solution was added into the SDS solution dropwise and generated tiny precipitates in the mixture solution. The mixture was concentrated under reduced pressure to form buprenorphine decanoate-SDS ionic complex. The ionic complex (6% w/w) was further mixed with sucrose acetate isobutyrate (SAIB, 38% w/w) and NMP (56% w/w) to form formulation BDSB1.

EXAMPLE 9

In Vitro Dissolution Test of Formulations

The formulations in examples 4-8 were further investigated for their in vitro dissolution profile. The dissolution medium composed of 1% sodium dodecyl sulfate and 0.02% sodium azide in phosphate buffered saline. The tubes were incubated in a reciprocal shaker at the rate of 60 rpm with 37° C. or 55° C. water bath simultaneously. The tubes were pulled, sampled as 1 mL solution, and then refilled with 1 mL fresh medium subsequently at specific timepoints. These samples were analyzed through HPLC for buprenorphine derivatives and their parent compound, i.e., buprenorphine free base. The in vitro releasing profiles are revealed in FIGS. 25 to 31 and Tables 11 to 18.

TABLE 11

In vitro dissolution % release of AS01-04

% Release at 55° C.

| Time (days) | AS01 | AS02 | AS03 | AS04 |
|---|---|---|---|---|
| 0 | 0.0 | 0.0 | 0.0 | 0.0 |
| 0.042 | 1.5 | 0.9 | 0.9 | 0.0 |
| 0.083 | 3.7 | 2.1 | 2.1 | 0.6 |
| 0.167 | 7.0 | 4.2 | 4.1 | 1.2 |
| 1 | 24.3 | 16.0 | 15.7 | 5.8 |
| 2 | 34.8 | 25.6 | 24.6 | 10.4 |
| 3 | 42.3 | 32.7 | 31.1 | 13.0 |
| 4 | 49.5 | 40.8 | 38.4 | 17.2 |
| 5 | 54.9 | 47.1 | 44.4 | 21.1 |
| 6 | 56.7 | 53.3 | 49.7 | 24.4 |
| 7 | 60.6 | 57.7 | 53.7 | 26.6 |
| 8 | 63.2 | 59.3 | 55.4 | 28.3 |
| 9 | 66.8 | 63.9 | 59.7 | 31.2 |
| 10 | 68.7 | 67.5 | 61.7 | 33.2 |
| 11 | 67.4 | 70.7 | 66.3 | 35.8 |
| 12 | 72.3 | 72.3 | 67.2 | 37.2 |
| 14 | 75.5 | 77.0 | 71.7 | 41.7 |
| 16 | 77.8 | 80.2 | 75.3 | 43.5 |
| 17 | 78.1 | 81.6 | 76.2 | 42.3 |
| 21 | 79.8 | 85.4 | 79.6 | 48.4 |
| 24 | 84.2 | 88.5 | 83.6 | 51.5 |
| 28 | 83.8 | 89.4 | 84.7 | 55.7 |
| 31 | 84.5 | 89.9 | 86.8 | 58.1 |
| 35 | 89.0 | 92.9 | 86.6 | 61.8 |

TABLE 12

In vitro dissolution % release of AS05-07

% Release at 55° C.

| Time (days) | AS05 | AS06 | Time (days) | AS07 |
|---|---|---|---|---|
| 0 | 0 | 0 | 0 | 0 |
| 0.042 | 7.6 | 9.3 | 0.042 | 58.00 |
| 0.083 | 11.8 | 15.0 | 0.167 | 90.67 |
| 0.167 | 18.1 | 24.9 | 1 | 102.33 |
| 1 | 42.0 | 61.1 | 2 | 103.92 |
| 2 | 49.4 | 75.3 | 5 | 101.94 |
| 5 | 60.8 | 82.0 | — | — |
| 6 | 66.9 | 88.0 | — | — |

TABLE 13

In vitro dissolution % release of AS08-09

% Release at 37° C.

| Time (hours) | AS08 | Time (hours) | AS09 |
|---|---|---|---|
| 0 | 0.24 | 0 | 0.00 |
| 1 | 56.5 | 0.5 | 80.39 |
| 2 | 60.0 | 1 | 97.96 |
| 4 | 65.6 | 2 | 99.98 |
| 6 | 69.1 | 4 | 101.69 |
| 8 | 71.7 | 6 | 99.96 |
| 24 | 80.9 | 8 | 102.72 |
| 48 | 99.7 | 24 | 105.61 |

TABLE 14

In vitro dissolution % release of MSA02 and MSA05

% Release at 37° C.

| Time (days) | MSA02 | MSA05 |
|---|---|---|
| 0 | 0.00 | 0.00 |
| 1 | 7.35 | 10.02 |
| 7 | 12.90 | 12.40 |
| 14 | 20.54 | 13.58 |
| 21 | 36.11 | 14.75 |
| 28 | 53.02 | 15.23 |
| 35 | 78.19 | 15.87 |
| 42 | 89.62 | 16.35 |
| 49 | 95.97 | 16.92 |
| 56 | 97.28 | 18.38 |
| 63 | — | 25.50 |
| 70 | — | 48.79 |
| 77 | — | 64.91 |
| 84 | — | 71.65 |

TABLE 15

In vitro dissolution % release of MSB01-05

% Release at 55° C.

| Time (days) | MSB01 | Time (days) | MSB02 | Time (days) | MSB03 | Time (days) | MSB04 | Time (days) | MSB05 |
|---|---|---|---|---|---|---|---|---|---|
| 0 | 0 | 0 | 0 | 0 | 0 | 0 | 0 | 0 | 0 |
| 0.042 | 12 | 0.042 | 6 | 0.042 | 1.3 | 0.042 | 19.1 | 0.042 | 3.4 |
| 0.083 | 12 | 0.083 | 8 | 0.083 | 2.3 | 0.083 | 23.1 | 0.083 | 3.5 |
| 0.167 | 14 | 0.146 | 11 | 0.167 | 3.9 | 0.167 | 26.4 | 0.146 | 3.7 |
| 1 | 20 | 1 | 30 | 1 | 13.1 | 1 | 45.8 | 1 | 4.9 |
| 2 | 25 | 2 | 46 | 2 | 19.9 | 2 | 56.6 | 3 | 10.0 |
| 3 | 29 | 3 | 55 | 3 | 26.7 | 3 | 59.5 | 7 | 18.5 |
| 4 | 33 | 6 | 67 | 4 | 36 | 5 | 70.6 | 8 | 18.0 |
| 7 | 46 | 9 | 68 | 5 | 40.5 | 6 | 70.5 | 9 | 19.7 |
| 8 | 50 | 13 | 68 | 6 | 44.5 | 7 | 71.9 | 10 | 22.7 |

TABLE 15-continued

In vitro dissolution % release of MSB01-05
% Release at 55° C.

| Time (days) | MSB01 | Time (days) | MSB02 | Time (days) | MSB03 | Time (days) | MSB04 | Time (days) | MSB05 |
|---|---|---|---|---|---|---|---|---|---|
| 9 | 55 | 21 | 68 | 8 | 48.5 | 8 | 74.2 | 11 | 26.4 |
| 10 | 58 | 27 | 70 | 10 | 58.1 | 9 | 75.3 | 15 | 33.5 |
| 11 | 63 | — | — | 14 | 72.2 | 10 | 76.5 | 21 | 42.5 |
| 14 | 69 | — | — | 21 | 95.4 | 13 | 73.4 | 28 | 55.3 |
| 17 | 70 | — | — | 24 | 97.1 | 16 | 78.8 | 36 | 72.4 |
| 21 | 75 | — | — | — | — | — | — | — | — |
| 24 | 77 | — | — | — | — | — | — | — | — |
| 29 | 80 | — | — | — | — | — | — | — | — |
| 35 | 83 | — | — | — | — | — | — | — | — |

TABLE 16

In vitro dissolution % release of PS01, PS02, PS09, and PS10
% Release at 55° C.

| Time (days) | PS01 | PS02 | Time (days) | PS09 | Time (days) | PS10 |
|---|---|---|---|---|---|---|
| 0 | 0 | 0 | 0 | 0 | 0 | 0 |
| 0.042 | 15 | 6 | 0.042 | 20.7 | 0.042 | 0.7 |
| 0.083 | 20 | 10 | 0.083 | 29.5 | 0.083 | 1.1 |
| 0.167 | 25 | 15 | 0.167 | 39.4 | 0.167 | 2.6 |
| 1 | 54 | 34 | 1 | 55.5 | 1 | 5.3 |
| 2 | 75 | 48 | 2 | 60 | 4 | 18.1 |
| 3 | 87 | 57 | 3 | 62.1 | 7 | 25.4 |
| 4 | 95 | 66 | 4 | 64.5 | 13 | 34.9 |
| 5 | 102 | 71 | 5 | 66.9 | 15 | 38.7 |
| 6 | — | 75 | — | — | 19 | 44.1 |
| 7 | — | 77 | — | — | 27 | 58 |
| 8 | — | 79 | — | — | — | — |
| 9 | — | 82 | — | — | — | — |
| 10 | — | 84 | — | — | — | — |
| 16 | — | 104 | — | — | — | — |

TABLE 17

In vitro dissolution % release of PS03-08
% Release at 55° C.

| Time (days) | PS03 | Time (days) | PS04 | Time (days) | PS05 | PS06 | PS07 | PS08 |
|---|---|---|---|---|---|---|---|---|
| 0 | 0 | 0 | 0 | 0 | 0 | 0 | 0 | 0 |
| 0.042 | 2 | 0.042 | 1 | 0.042 | 0.9 | 0.9 | 0.7 | 0.4 |
| 0.083 | 2 | 0.083 | 1 | 0.083 | 1.2 | 1.4 | 1.1 | 0.4 |
| 0.167 | 2 | 1 | 5 | 0.167 | 2.1 | 2.4 | 2 | 0.8 |
| 1 | 8 | 2 | 9 | 1 | 10.1 | 8.7 | 8.9 | 2.9 |
| 2 | 12 | 7 | 27 | 2 | 18.7 | 14 | 15.2 | 5.1 |
| 3 | 17 | 9 | 31 | 3 | 26.6 | 19 | 21 | 7.4 |
| 5 | 25 | 12 | 43 | 5 | 37.8 | 26.7 | 28.6 | 11.8 |
| 6 | 28 | 13 | 46 | 6 | 42 | 30.1 | 31.7 | 14.2 |
| 7 | 32 | 15 | 50 | 7 | 45.9 | 33.4 | 34.8 | 16.6 |
| 8 | 36 | 19 | 59 | 8 | 48.7 | 36 | 37 | 19.2 |
| 9 | 40 | 22 | 62 | 9 | 51.7 | 39 | 39.4 | 21.8 |
| 14 | 65 | 26 | 64 | 12 | 58.6 | 46.7 | 47.5 | 27.6 |
| 19 | 85 | 29 | 69 | 19 | 68.2 | 58.5 | 60.6 | 37.8 |
| 22 | 91 | 35 | 75 | 26 | 75 | 69.3 | 73.3 | 46.4 |
| 26 | 95 | 37 | 73 | 33 | 76.4 | 74.6 | 80.1 | 52.1 |
| — | — | 40 | 82 | 41 | 79 | 79.7 | 83.9 | 58.5 |
| — | — | 43 | 84 | 47 | 79.4 | 81.8 | 83.8 | 62.4 |
| — | — | 47 | 84 | 54 | 77.2 | 84.3 | 84.5 | 65 |
| — | — | 50 | 86 | — | — | — | — | — |
| — | — | 54 | 87 | — | — | — | — | — |
| — | — | 57 | 85 | — | — | — | — | — |
| — | — | 61 | 88 | — | — | — | — | — |
| — | — | 65 | 90 | — | — | — | — | — |

TABLE 18

In vitro dissolution % release of BDSB1, LS01-04
% Release at 55° C.

| Time (days) | BDSB1 | Time (days) | LS01 | LS02 | Time (days) | LS03 | LS04 |
|---|---|---|---|---|---|---|---|
| 0 | 0 | 0 | 0 | 0 | 0 | 0 | 0 |
| 0.042 | 1 | 0.063 | 1.98 | 0.00 | 0.125 | 5.48 | 0.50 |
| 0.083 | 1 | 0.208 | 5.12 | 3.40 | 0.271 | 8.58 | 1.75 |
| 0.167 | 2 | 1 | 19.7 | 6.85 | 1 | 15.5 | 4.82 |
| 1 | 3 | 2 | 28.9 | 7.10 | 2 | 23.8 | 9.16 |
| 2 | 5 | 3 | 35.4 | 7.75 | 5 | 50.6 | 12.1 |
| 6 | 13 | 6 | 60.0 | 9.85 | 8 | 70.6 | 14.5 |
| 7 | 16 | 10 | 75.3 | 21.9 | 12 | 88.2 | 17.4 |
| 8 | 17 | 13 | 84.1 | 24.6 | 15 | 94.8 | 19.7 |
| 10 | 20 | 16 | 87.1 | 26.0 | 20 | 100.7 | 21.8 |
| 14 | 26 | 20 | 89.7 | 29.2 | — | — | — |
| 22 | 32 | 24 | 99.2 | 32.2 | — | — | — |
| 27 | 35 | 28 | — | 33.8 | — | — | — |
| 35 | 42 | — | — | — | — | — | — |
| 42 | 47 | — | — | — | — | — | — |
| 48 | 50 | — | — | — | — | — | — |

EXAMPLE 10

Figure 32:
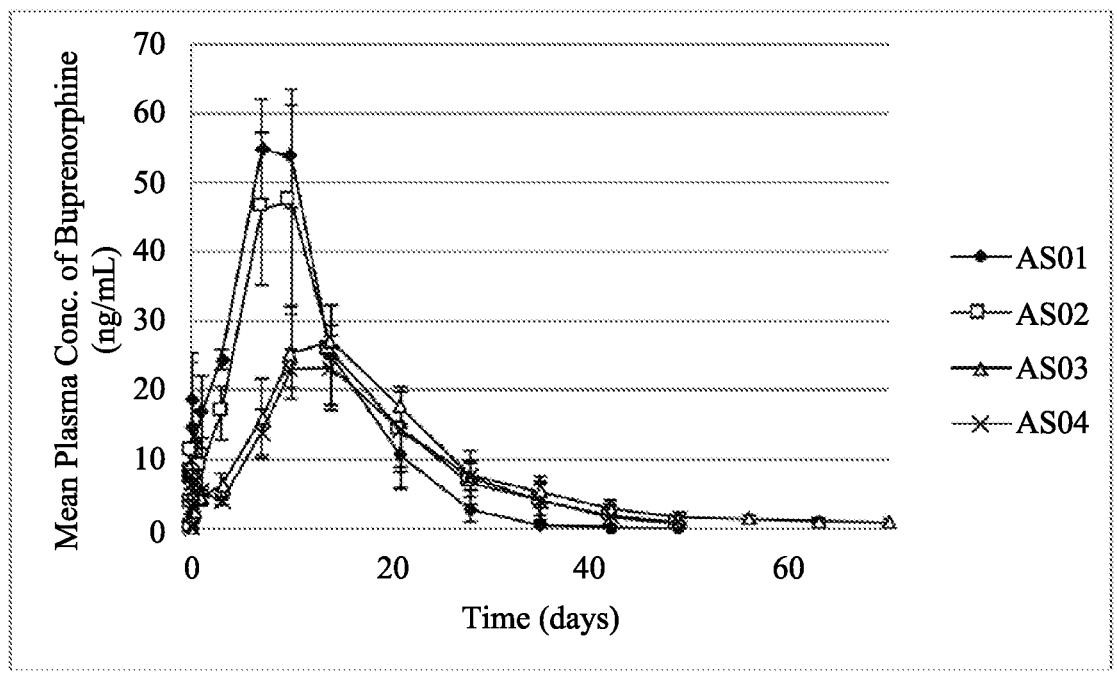
FIG. 32 illustrates the pharmacokinetic (PK) profile of AS01-04 in rats.
Figure 33:
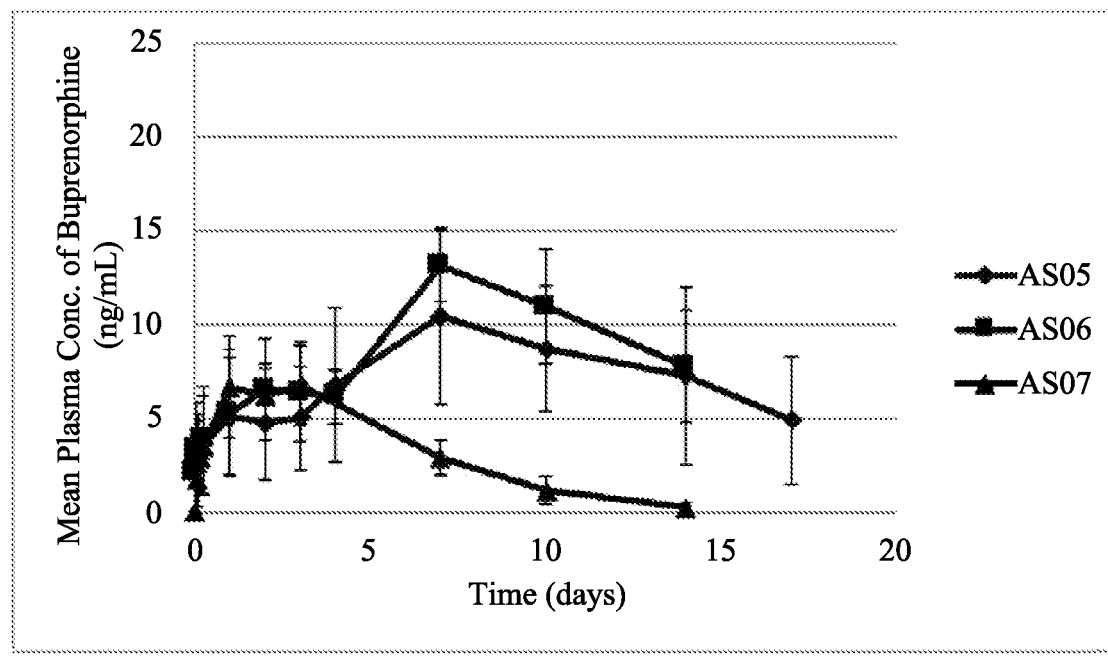
FIG. 33 illustrates the PK profile of AS05-07 in rats.
Figure 34:
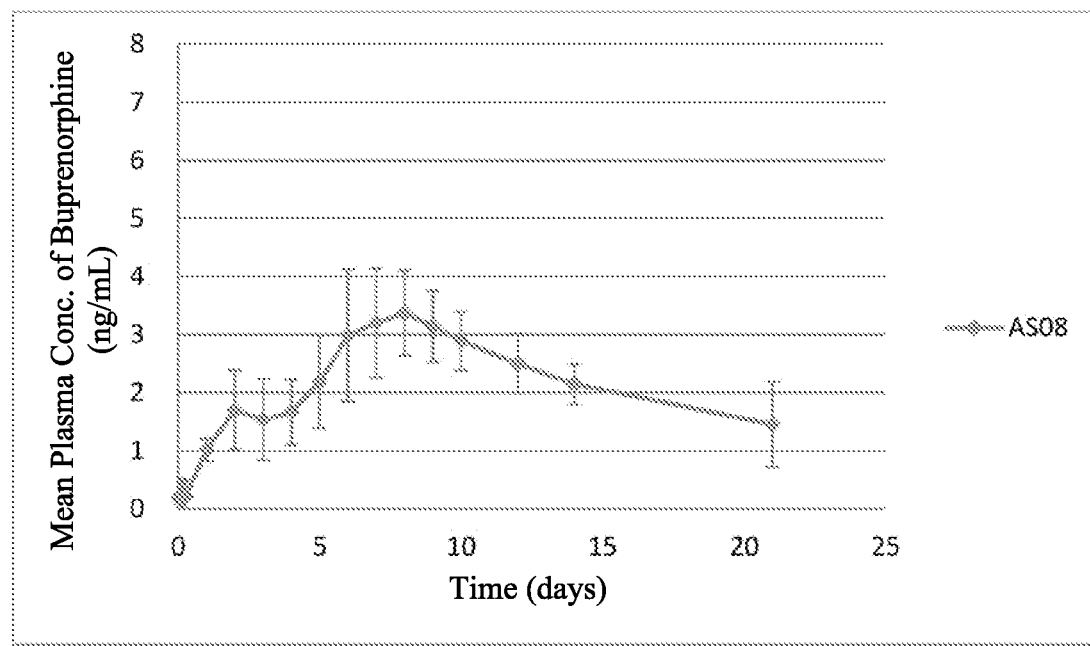
FIG. 34 illustrates the PK profile of AS08 in minipigs.

Pharmacokinetic Profile of Aqueous Suspension of Buprenorphine Derivatives in Rats and Minipigs The aqueous suspension formulations of buprenorphine derivatives in Example 4 were administered subcutaneously or intramuscularly in SD male rats at a dose of 60 mg/kg buprenorphine equivalent. The resulted mean plasma concentrations of buprenorphine versus time profiles were shown in FIGS. 32-33 and Tables 19-20. Formulation AS08 was injected in Lanyu male minipigs subcutaneously. The mean plasma concentrations of buprenorphine versus time profiles are shown in FIG. 34 and Table 21.

TABLE 19

Mean plasma concentrations of buprenorphine after injection in rats

| | AS01 | | AS02 | | AS03 | | AS04 | |
|---|---|---|---|---|---|---|---|---|
| Time (days) | Mean (ng/mL) | S.D. (n = 3) | Mean (ng/mL) | S.D. (n = 3) | Mean (ng/mL) | S.D. (n = 3) | Mean (ng/mL) | S.D (n = 3) |
| 0 | 0.04 | 0.07 | 0.00 | 0.00 | 0.00 | 0.00 | 0.00 | 0.00 |
| 0.021 | 14.61 | 9.36 | 3.59 | 0.86 | 1.89 | 0.20 | 3.40 | 3.30 |
| 0.042 | 18.5 | 6.94 | 11.4 | 5.84 | 4.92 | 3.08 | 6.93 | 1.50 |
| 0.083 | 9.51 | 2.72 | 7.25 | 2.54 | 2.12 | 0.56 | 10.0 | 1.95 |
| 0.17 | 11.63 | 1.42 | 8.01 | 3.48 | 1.67 | 0.40 | 7.41 | 1.18 |
| 0.25 | 12.32 | 2.63 | 7.25 | 2.09 | 2.13 | 0.30 | 6.71 | 3.02 |

TABLE 19-continued

Mean plasma concentrations of buprenorphine after injection in rats

| Time (days) | AS01 Mean (ng/mL) | S.D. (n = 3) | AS02 Mean (ng/mL) | S.D. (n = 3) | AS03 Mean (ng/mL) | S.D. (n = 3) | AS04 Mean (ng/mL) | S.D (n = 3) |
|---|---|---|---|---|---|---|---|---|
| 1 | 16.8 | 5.28 | 9.05 | 4.06 | 4.67 | 1.37 | 5.25 | 0.35 |
| 3 | 24.5 | 1.42 | 16.7 | 3.87 | 6.15 | 1.87 | 3.95 | 0.56 |
| 7 | 54.9 | 7.28 | 46.3 | 11.1 | 15.9 | 5.8 | 14.0 | 3.27 |
| 10 | 53.8 | 7.46 | 47.2 | 16.3 | 25.4 | 6.67 | 23.1 | 2.81 |
| 14 | 25.1 | 7.15 | 25.6 | 0.96 | 27.1 | 0.66 | 23.3 | 6.09 |
| 21 | 10.5 | 4.61 | 14.3 | 6.07 | 17.6 | 3.02 | 14.3 | 5.48 |
| 28 | 2.73 | 1.78 | 6.56 | 2.99 | 7.74 | 2.22 | 7.42 | 3.88 |
| 35 | 0.52 | 0.41 | 4.2 | 2.28 | 5.28 | 2.23 | 4.00 | 2.80 |
| 42 | 0.23 | 0.22 | 1.66 | 1.07 | 2.87 | 1.15 | 1.94 | 1.64 |
| 49 | 0.00 | 0.00 | 0.68 | 0.36 | 1.62 | 0.82 | 0.88 | 0.77 |
| 56 | — | — | — | — | 1.41 | 0.54 | — | — |
| 63 | — | — | — | — | 1.17 | 0.40 | — | — |
| 70 | — | — | — | — | 0.89 | 0.47 | — | — |

TABLE 20

Mean plasma concentrations of buprenorphine after injection in rats

| Time (days) | AS05 Mean (ng/mL) | S.D. (n = 4) | AS06 Mean (ng/mL) | S.D. (n = 4) | Time (days) | AS07 Mean (ng/mL) | S.D. (n = 3) |
|---|---|---|---|---|---|---|---|
| 0 | 3.26 | 0.07 | 2.02 | 2.39 | 0 | 0 | 0 |
| 0.042 | 3.04 | 1.82 | 3.09 | 2.77 | 0.083 | 1.72 | 0.63 |
| 0.083 | 2.73 | 1.55 | 3.27 | 1.93 | 0.167 | 2.82 | 0.65 |
| 0.25 | 3.59 | 2.64 | 3.84 | 2.85 | 0.25 | 3.54 | 0.68 |
| 1 | 5.11 | 3.13 | 5.30 | 3.36 | 1 | 6.69 | 2.68 |
| 2 | 4.83 | 3.10 | 6.54 | 2.70 | 2 | 6.18 | 1.48 |
| 3 | 5.01 | 2.76 | 6.40 | 2.65 | 3 | 6.78 | 2.13 |
| 4 | 6.79 | 4.10 | 6.15 | 1.42 | 7 | 2.92 | 0.92 |
| 7 | 10.5 | 4.69 | 13.1 | 1.88 | 10 | 1.21 | 0.75 |
| 10 | 8.73 | 3.32 | 11.0 | 3.05 | 14 | 0.27 | 0.23 |
| 14 | 7.25 | 4.72 | 7.78 | 2.97 | — | — | — |
| 17 | 4.90 | 3.41 | 4.07 | 3.35 | — | — | — |

TABLE 21

Mean plasma concentrations of buprenorphine after injection in minipig

| | AS08 | |
|---|---|---|
| Time (days) | Mean (ng/mL) | S.D. (n = 3) |
| 0 | 0.177 | 0.21 |
| 0.08 | 0.228 | 0.30 |
| 0.17 | 0.227 | 0.28 |
| 0.25 | 0.217 | 0.26 |
| 1 | 1.01 | 0.20 |
| 2 | 1.70 | 0.69 |
| 3 | 1.54 | 0.70 |
| 4 | 1.66 | 0.57 |
| 5 | 2.19 | 0.80 |
| 6 | 2.98 | 1.14 |
| 7 | 3.20 | 0.93 |
| 8 | 3.37 | 0.73 |
| 9 | 3.15 | 0.61 |
| 10 | 2.89 | 0.50 |
| 12 | 2.51 | 0.51 |
| 14 | 2.15 | 0.35 |
| 21 | 1.46 | 0.73 |

EXAMPLE 11

Figure 35:
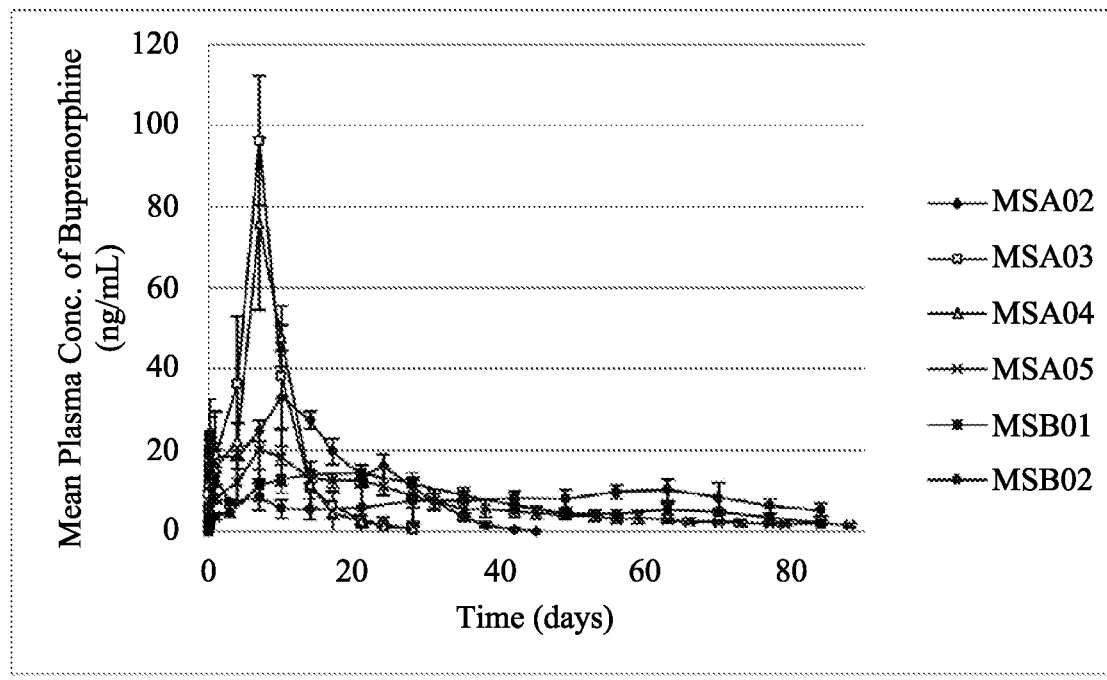
FIG. 35 illustrates the PK profile of MSA02-05 and MSB01-02 in rats.

Pharmacokinetic Profile of Aqueous Suspension of Microspheres Containing Buprenorphine Derivatives in Rats and Dogs Four buprenorphine decanoate citric acid salt-containing microspheres formulations as shown in Example 5 were prepared as suspension at a concentration of 100 to 150 mg/mL. The diluent was composed of 10 mM phosphate-buffered saline, 1.25% sodium carboxymethylcellulose, and 0.05% Tween 80. The suspension formulations were intramuscularly or subcutaneously injected in SD male rats at dose of 60 mg/kg buprenorphine equivalent. The pharmacokinetic profile results are shown in FIG. 35 and Tables 22-23.

TABLE 22

Mean plasma buprenorphine levels after intramuscular injection of MSA02-05 in rats

| Time (Day) | MSA02 Mean (ng/mL) | S.D. (n = 3) | MSA03 Mean (ng/mL) | S.D. (n = 3) | MSA04 Mean (ng/mL) | S.D. (n = 3) | MSA05 Mean (ng/mL) | S.D. (n = 3) |
|---|---|---|---|---|---|---|---|---|
| 0 | 0.03 | 0.05 | 0.21 | 0.37 | 0.32 | 0.28 | 0.09 | 0.01 |
| 0.007 | 1.18 | 0.24 | 2.10 | 0.73 | 4.26 | 2.27 | 1.45 | 0.60 |
| 0.021 | 2.41 | 0.95 | 5.30 | 1.03 | 6.36 | 2.05 | 3.18 | 0.87 |
| 0.042 | 5.93 | 2.2 | 9.23 | 1.99 | 12.1 | 1.49 | 6.26 | 1.01 |
| 0.083 | 13.9 | 4.02 | 13.0 | 1.74 | 16.3 | 3.02 | 14.3 | 0.95 |
| 0.167 | 20.4 | 2.27 | 16.1 | 2.22 | 19.2 | 1.12 | 22.0 | 2.44 |
| 0.25 | 22.4 | 2.74 | 15.6 | 1.57 | 20.4 | 7.90 | 20.1 | 3.16 |
| 1 | 18.8 | 2.86 | 18.7 | 11.0 | 15.6 | 4.48 | 8.13 | 1.02 |
| 4 | 18.30 | 2.84 | 36.4 | 16.6 | 22.2 | 4.54 | 12.31 | 5.09 |
| 7 | 24.8 | 2.55 | 96.2 | 15.90 | 75.8 | 21.3 | 20.2 | 7.30 |
| 10 | 33.0 | 7.60 | 38.4 | 17.30 | 47.7 | 3.15 | 18.2 | 6.77 |
| 14 | 27.47 | 2.12 | 10.8 | 2.65 | 11.6 | 5.69 | 13.0 | 1.04 |
| 17 | 19.7 | 3.05 | 6.43 | 3.18 | 4.72 | 5.09 | 12.6 | 1.92 |
| 21 | 13.7 | 2.57 | 2.98 | 1.24 | 2.42 | 3.24 | 12.4 | 0.75 |
| 24 | 16.1 | 3.00 | 1.53 | 0.56 | 1.49 | 2.16 | 11.1 | 2.16 |
| 28 | 11.0 | 2.40 | 0.80 | 0.71 | 0.81 | 1.02 | 8.69 | 2.68 |

TABLE 22-continued

Mean plasma buprenorphine levels after intramuscular injection of MSA02-05 in rats

| Time (Day) | MSA02 Mean (ng/mL) | MSA02 S.D. (n = 3) | MSA03 Mean (ng/mL) | MSA03 S.D. (n = 3) | MSA04 Mean (ng/mL) | MSA04 S.D. (n = 3) | MSA05 Mean (ng/mL) | MSA05 S.D. (n = 3) |
|---|---|---|---|---|---|---|---|---|
| 31 | 7.59 | 1.83 | — | — | — | — | 7.74 | 2.46 |
| 35 | 3.62 | 0.93 | — | — | — | — | 5.54 | 1.75 |
| 38 | 1.67 | 0.54 | — | — | — | — | 5.77 | 2.26 |
| 42 | 0.49 | 0.46 | — | — | — | — | 5.03 | 1.43 |
| 45 | 0.21 | 0.21 | — | — | — | — | 4.70 | 1.47 |
| 49 | — | — | — | — | — | — | 4.04 | 1.03 |
| 53 | — | — | — | — | — | — | 3.98 | 1.23 |
| 56 | — | — | — | — | — | — | 2.98 | 0.61 |
| 59 | — | — | — | — | — | — | 3.55 | 1.55 |
| 63 | — | — | — | — | — | — | 2.86 | 0.57 |
| 66 | — | — | — | — | — | — | 2.52 | 0.77 |
| 70 | — | — | — | — | — | — | 2.37 | 0.38 |
| 73 | — | — | — | — | — | — | 2.20 | 0.70 |
| 77 | — | — | — | — | — | — | 2.02 | 0.30 |
| 79 | — | — | — | — | — | — | 1.90 | 0.39 |
| 84 | — | — | — | — | — | — | 2.14 | 0.18 |
| 88 | — | — | — | — | — | — | 1.71 | 0.43 |

TABLE 23

Mean plasma buprenorphine levels after subcutaneous injection of MSB01-02 in rats

| Time (days) | MSB01 Mean (ng/mL) | MSB01 S.D. (n = 4) | MSB02 Mean (ng/mL) | MSB02 S.D. (n = 4) |
|---|---|---|---|---|
| 0 | 0.00 | 0.00 | 0.00 | 0.00 |
| 0.042 | 1.04 | 0.64 | 6.32 | 2.80 |
| 0.083 | 2.01 | 0.68 | 18.8 | 5.97 |
| 0.25 | 3.09 | 0.63 | 24.2 | 8.30 |
| 1 | 3.88 | 0.99 | 13.2 | 1.59 |
| 3 | 4.78 | 1.06 | 7.22 | 0.70 |
| 7 | 11.4 | 3.84 | 8.63 | 3.25 |
| 10 | 13.0 | 3.54 | 5.67 | 2.24 |
| 14 | 14.2 | 0.79 | 5.47 | 2.58 |
| 21 | 14.4 | 1.90 | 6.04 | 4.94 |
| 28 | 11.7 | 2.74 | 7.58 | 5.38 |
| 35 | 9.01 | 1.05 | 7.64 | 3.13 |
| 42 | 6.54 | 1.78 | 8.31 | 1.61 |
| 49 | 4.43 | 0.85 | 8.19 | 2.16 |
| 56 | 4.41 | 0.24 | 9.74 | 1.58 |
| 63 | 5.53 | 1.37 | 10.2 | 2.67 |
| 70 | 4.78 | 0.64 | 8.45 | 3.55 |
| 77 | 3.51 | 1.04 | 6.30 | 1.82 |
| 84 | 2.02 | 0.54 | 5.39 | 1.62 |

TABLE 24

Mean plasma buprenorphine levels after intramuscular injection in dogs

| Time (day) | MSA01 Mean (ng/mL) | MSA01 Standard deviation | MSA02 Mean (ng/mL) | MSA02 Standard deviation | MSA05 Mean (ng/mL) | MSA05 Standard deviation |
|---|---|---|---|---|---|---|
| 0 | 0.0 | 0.0 | 0.0 | 0.0 | 0.0 | 0.0 |
| 0.04 | 0.0 | 0.0 | 0.6 | 0.2 | 0.5 | 0.1 |
| 0.08 | 0.1 | 0.1 | 0.8 | 0.1 | 1.4 | 0.8 |
| 0.17 | 0.6 | 0.1 | 2.0 | 0.6 | 2.8 | 1.3 |
| 0.25 | 1.5 | 0.2 | 3.7 | 0.9 | 3.5 | 3.7 |
| 1 | 7.0 | 5.0 | 15.6 | 1.4 | 14.2 | 10.3 |
| 3 | 10.1 | 5.4 | 16.8 | 5.7 | 12.7 | 8.0 |
| 7 | 16.1 | 12.4 | 11.6 | 4.3 | 11.9 | 7.8 |
| 10 | 14.2 | 6.0 | 14.1 | 4.1 | 11.9 | 6.0 |
| 14 | 14.4 | 1.9 | 14.7 | 3.1 | 10.1 | 4.8 |
| 21 | 10.6 | 1.5 | 15.2 | 4.9 | 6.6 | 3.8 |
| 28 | 9.3 | 4.4 | 11.8 | 1.5 | 6.7 | 3.4 |
| 35 | 5.3 | 1.6 | 8.4 | 4.5 | 6.0 | 3.0 |
| 42 | 4.9 | 2.4 | 4.4 | 0.8 | 4.1 | 2.3 |
| 49 | 5.8 | 5.2 | 1.7 | 0.6 | 4.2 | 3.0 |
| 56 | 1.6 | 1.3 | 0.7 | 0.9 | 2.5 | 1.3 |
| 63 | 1.4 | 1.1 | 0.4 | 0.7 | 3.1 | 1.2 |
| 70 | 0.5 | 0.7 | 0.0 | 0.0 | 2.5 | 1.1 |
| 77 | 0.6 | 0.6 | 0.3 | 0.5 | 2.4 | 1.2 |
| 84 | 0.5 | 0.7 | 0.0 | 0.0 | 1.9 | 1.1 |
| 91 | 0.4 | 0.4 | 0.1 | 0.2 | 0.9 | 1.0 |

Figure 36:
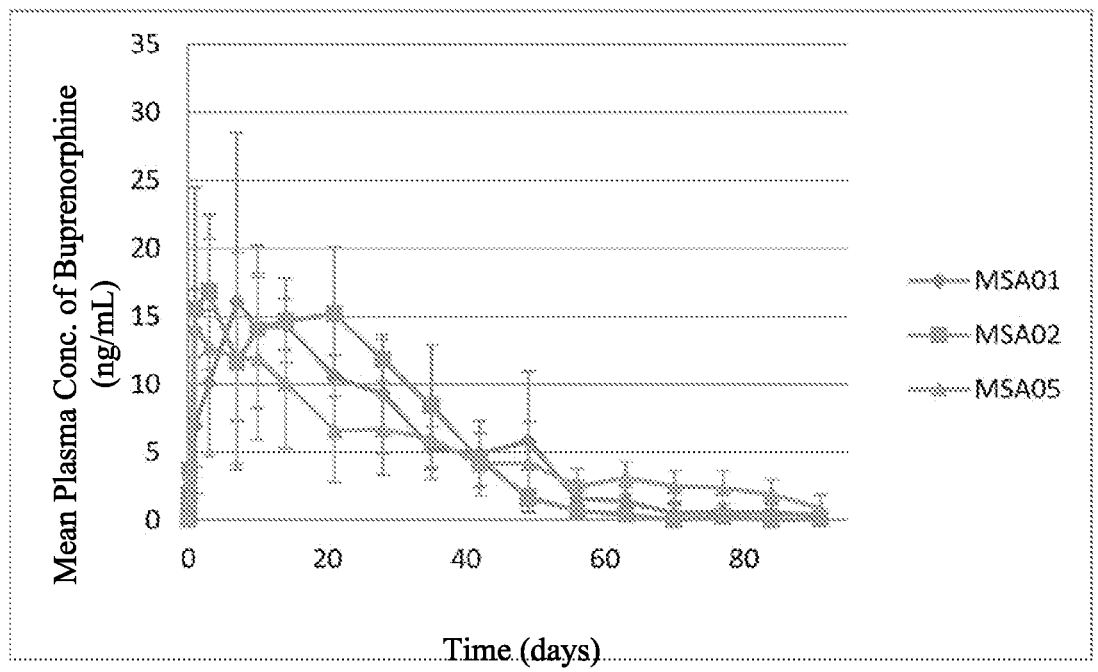
FIG. 36 illustrates the PK profile of MSA01, MSA02, and MSA05 in dogs.

Three buprenorphine decanoate and citric acid salt thereof contained microspheres formulations as shown in Example 5 were prepared as suspension at the concentration of 300 mg/mL. The diluent was composed of 10 mM phosphate-buffered saline, 1.25% sodium carboxymethylcellulose, and 0.05% Tween 80. The suspension formulations were intramuscularly injected in beagle dogs at dose of 18.9 mg/kg buprenorphine equivalent. The pharmacokinetic profile results are shown in FIG. 36 and Table 24.

EXAMPLE 12

Pharmacokinetic Profile of PLGA-Based Formulations in Rats

Figure 37:
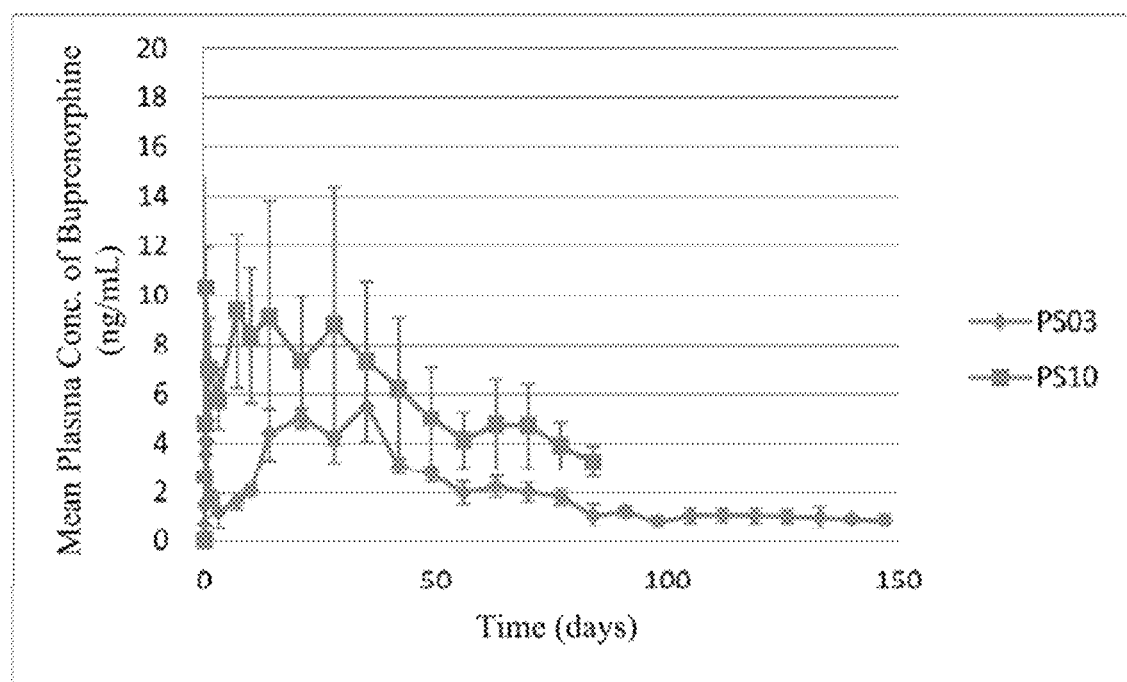
FIG. 37 illustrates the PK profile of PS03 and PS10 in rats.

The PLGA-based formulations, PS03 and PS10, as prepared in Example 6 were injected subcutaneously or in SD male rats at a dose of 60 mg/kg buprenorphine equivalent. The pharmacokinetic profile results are shown in FIG. 37 and Table 25.

TABLE 25

Mean plasma buprenorphine levels after intramuscular injection in rats

| | PS03 | | | PS10 | |
|---|---|---|---|---|---|
| Time (days) | Mean (ng/mL) | S.D. (n = 3) | Time (days) | Mean (ng/mL) | S.D. (n = 4) |
| 0 | 0.00 | 0.00 | 0 | 0.00 | 0.00 |
| 0.021 | 0.070 | 0.12 | 0.042 | 2.67 | 0.23 |
| 0.042 | 0.690 | 0.38 | 0.083 | 4.76 | 0.87 |
| 0.083 | 1.51 | 0.78 | 0.25 | 10.3 | 1.63 |
| 0.17 | 3.58 | 0.92 | 1 | 6.98 | 2.08 |
| 0.25 | 4.07 | 2.65 | 3 | 5.78 | 1.23 |
| 1 | 1.76 | 0.33 | 7 | 9.39 | 3.13 |
| 3 | 1.23 | 0.72 | 10 | 8.39 | 2.73 |
| 7 | 1.66 | 0.32 | 14 | 9.11 | 4.73 |
| 10 | 2.06 | 0.23 | 21 | 7.31 | 2.63 |
| 14 | 4.38 | 1.06 | 28 | 8.80 | 5.57 |
| 21 | 5.02 | 0.45 | 35 | 7.32 | 3.27 |
| 28 | 4.21 | 0.26 | 42 | 6.22 | 2.85 |
| 35 | 5.52 | 1.48 | 49 | 5.03 | 2.03 |
| 42 | 3.09 | 0.35 | 56 | 4.13 | 1.10 |
| 49 | 2.75 | 0.32 | 63 | 4.75 | 1.81 |
| 56 | 1.99 | 0.46 | 70 | 4.70 | 1.69 |
| 63 | 2.23 | 0.43 | 77 | 3.90 | 0.92 |
| 70 | 2.01 | 0.38 | 84 | 3.27 | 0.61 |
| 77 | 1.83 | 0.31 | — | — | — |
| 84 | 1.09 | 0.45 | — | — | — |
| 91 | 1.25 | 0.22 | — | — | — |
| 98 | 0.830 | 0.25 | — | — | — |
| 105 | 1.09 | 0.32 | — | — | — |
| 112 | 1.10 | 0.29 | — | — | — |
| 119 | 1.09 | 0.31 | — | — | — |
| 126 | 1.04 | 0.26 | — | — | — |
| 133 | 1.02 | 0.44 | — | — | — |
| 140 | 0.950 | 0.12 | — | — | — |
| 147 | 0.870 | 0.23 | — | — | — |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

What is claimed is:

1. A crystalline form of 3-acyl-buprenorphine represented by Formula II:

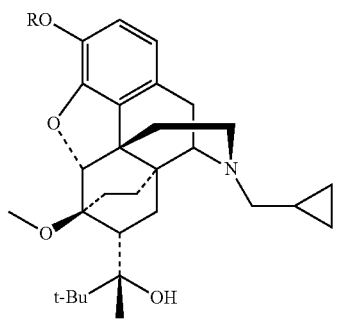

(II)

wherein R is an acyl group having a straight chain or a branched chain alkyl portion of 1 to 17 carbon atoms, and the crystalline form is characterized by an X-ray powder diffraction pattern comprising peaks at 4.70, 8.44, 9.38, 20.56, or peaks at 6.03, 9.08, 9.58, 9.68, or peaks at 5.98, 9.43, 11.83, 11.93, or peaks at 7.53, 8.13, 13.48, 16.03, or peaks at 5.80, 8.00, 11.50, 17.34 or peaks at 5.68, 8.03, 11.38, 17.23 degrees 2θ±0.2 degrees 2θ.

2. The crystalline form of claim 1, wherein the 3-acyl-buprenorphine is buprenorphine acetate having an X-ray powder diffraction pattern in accordance with that shown in FIG. 1, or wherein the 3-acyl-buprenorphine is buprenorphine pivalate having an X-ray powder diffraction pattern in accordance with that shown in FIG. 5, or wherein the 3-acyl-buprenorphine is buprenorphine pentanoate having an X-ray powder diffraction pattern in accordance with that shown in FIG. 9, or wherein the 3-acyl-buprenorphine is buprenorphine hexanoate having an X-ray powder diffraction pattern in accordance with that shown in FIG. 13, or wherein the 3-acyl-buprenorphine is buprenorphine decanoate having an X-ray powder diffraction pattern in accordance with that shown in FIG. 17, or wherein the 3-acyl-buprenorphine is buprenorphine dodecanoate having an X-ray powder diffraction pattern in accordance with that shown in FIG. 21.

3. A sustained release pharmaceutical composition comprising the crystalline form of claim 1, and a pharmaceutically acceptable carrier thereof.

4. An aqueous injectable pharmaceutical suspension comprising the crystalline form of claim 1, or a pharmaceutically acceptable salt thereof, in a suspending aqueous diluent, exhibiting a steady release profile lasting over at least one week when injected into a patient or an animal and without including an organic solvent, a polylactide polymer, a polyglycolide polymer, or a copolymer of polylactide and polyglycolide.

5. The injectable pharmaceutical suspension according to claim 4, having an average particle size of less than 80 μm.

6. The injectable pharmaceutical suspension according to claim 4, wherein the suspending aqueous diluent comprising a polyethylene glycol polymer and polysorbate in phosphate buffered saline.

7. The injectable pharmaceutical suspension according to claim 4, wherein the 3-acyl-buprenorphine or a pharmaceutically acceptable salt thereof is present at a concentration of 5% to 30% w/w.

8. A method for treating opioid addiction, pain or depression, the method comprising administrating the aqueous injectable pharmaceutical suspension according to claim 4 to a subject in need thereof subcutaneously or intramuscularly with a therapeutically effective duration of at least one week.

* * * * *